United States Patent
Braido et al.

(10) Patent No.: US 12,023,240 B2
(45) Date of Patent: *Jul. 2, 2024

(54) BOWED RUNNERS AND CORRESPONDING VALVE ASSEMBLIES FOR PARAVALVULAR LEAK PROTECTION

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L McCarthy, Vadnais Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 544 days.

This patent is subject to a terminal disclaimer.

(21) Appl. No.: 17/185,310

(22) Filed: Feb. 25, 2021

(65) Prior Publication Data
US 2021/0177591 A1 Jun. 17, 2021

Related U.S. Application Data

(63) Continuation of application No. 16/299,969, filed on Mar. 12, 2019, now Pat. No. 10,952,847, which is a
(Continued)

(51) Int. Cl.
*A61F 2/24* (2006.01)
*A61F 2/966* (2013.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC ........ A61F 2/24; A61F 2/2418; A61F 2/2409; A61F 2/2412; A61F 2/2475
See application file for complete search history.

(56) References Cited

U.S. PATENT DOCUMENTS

| 5,397,355 A | 3/1995 | Marin et al. |
| 6,517,573 B1 | 2/2003 | Pollock et al. |

(Continued)

FOREIGN PATENT DOCUMENTS

| WO | 2007058857 A2 | 5/2007 |
| WO | 2010008548 A2 | 1/2010 |

(Continued)

OTHER PUBLICATIONS

International Search Report for Application No. PCT/US2015/015533 dated Apr. 28, 2015.

*Primary Examiner* — Alvin J Stewart
(74) *Attorney, Agent, or Firm* — SLEMAN & LUND LLP

(57) ABSTRACT

A prosthetic heart valve for replacing a native valve includes a stent extending between a proximal end and a distal end and including a plurality of struts forming cells, the stent having a collapsed condition and an expanded condition. At least one runner is coupled a cell, the at least one runner being configured to transition from a first configuration to a second configuration when the stent moves from the collapsed condition to the expanded condition, the at least one runner projecting radially outwardly from the cell in the second configuration. A valve assembly is disposed within the stent, the valve assembly including a plurality of leaflets, a cuff at least partially disposed on a luminal surface of the stent, and a covering material disposed on an abluminal surface of the stent and covering the at least one runner in the second configuration.

20 Claims, 22 Drawing Sheets

Related U.S. Application Data continuation of application No. 15/921,106, filed on Mar. 14, 2018, now Pat. No. 10,271,946, which is a continuation of application No. 15/118,991, filed as application No. PCT/US2015/015533 on Feb. 12, 2015, now Pat. No. 9,949,825.

(60) Provisional application No. 61/941,012, filed on Feb. 18, 2014.

(52) U.S. Cl.
CPC ...... *A61F 2/966* (2013.01); *A61F 2230/0013* (2013.01); *A61F 2230/0017* (2013.01); *A61F 2230/0078* (2013.01); *A61F 2250/0039* (2013.01); *A61F 2250/0069* (2013.01)

(56) References Cited

U.S. PATENT DOCUMENTS

| | | | | |
|---|---|---|---|---|
| 8,092,520 | B2 | 1/2012 | Quadri | |
| 8,403,983 | B2* | 3/2013 | Quadri | A61F 2/2412 623/2.14 |
| 8,454,686 | B2 | 6/2013 | Alkhatib | |
| 8,579,964 | B2 | 11/2013 | Lane et al. | |
| 8,628,566 | B2 | 1/2014 | Eberhardt et al. | |
| 8,652,203 | B2 | 2/2014 | Quadri et al. | |
| 8,652,204 | B2 | 2/2014 | Quill et al. | |
| 8,673,000 | B2 | 3/2014 | Tabor et al. | |
| 8,685,086 | B2 | 4/2014 | Navia et al. | |
| 8,790,395 | B2 | 7/2014 | Straubinger et al. | |
| 8,834,563 | B2* | 9/2014 | Righini | A61F 2/2436 623/2.18 |
| 8,834,564 | B2 | 9/2014 | Tuval et al. | |
| 8,840,661 | B2 | 9/2014 | Manasse | |
| 8,961,595 | B2 | 2/2015 | Alkhatib | |
| 8,986,375 | B2* | 3/2015 | Garde | A61F 2/2418 623/2.38 |
| 9,023,100 | B2 | 5/2015 | Quadri et al. | |
| 9,186,249 | B2 | 11/2015 | Rolando et al. | |
| D755,384 | S* | 5/2016 | Pesce | D24/155 |
| 9,333,073 | B2 | 5/2016 | Quadri et al. | |
| 9,398,951 | B2* | 7/2016 | Alkhatib | A61F 2/2418 |
| 9,480,560 | B2 | 11/2016 | Quadri et al. | |
| 9,603,705 | B2 | 3/2017 | Alkhatib | |
| 9,668,857 | B2* | 6/2017 | Braido | A61F 2/2418 |
| 9,668,858 | B2* | 6/2017 | Morin | A61F 2/2418 |
| 9,681,951 | B2 | 6/2017 | Ratz et al. | |
| 9,730,790 | B2 | 8/2017 | Quadri et al. | |
| 9,750,607 | B2 | 9/2017 | Ganesan et al. | |
| 9,867,697 | B2* | 1/2018 | Alkhatib | A61F 2/2418 |
| 9,949,825 | B2* | 4/2018 | Braido | A61F 2/2418 |
| 10,130,467 | B2* | 11/2018 | Braido | A61F 2/2418 |
| 10,166,097 | B2* | 1/2019 | Quadri | A61F 2/2427 |
| D841,812 | S | 2/2019 | Hariton et al. | |
| D841,813 | S* | 2/2019 | Hariton | A61F 2/2412 D24/155 |
| 10,213,307 | B2* | 2/2019 | Dwork | A61F 2/2469 |
| 10,271,946 | B2* | 4/2019 | Braido | A61F 2/966 |
| 10,271,949 | B2* | 4/2019 | Dakin | A61F 2/2418 |
| 10,413,401 | B2* | 9/2019 | Eberhardt | A61F 2/2409 |
| 10,456,249 | B2* | 10/2019 | Kaleta | A61F 2/2412 |
| 10,575,948 | B2 | 3/2020 | Iamberger et al. | |
| 10,856,971 | B2* | 12/2020 | Maimon | A61F 2/2418 |
| 10,856,975 | B2* | 12/2020 | Hariton | B23P 15/001 |
| 10,888,420 | B2* | 1/2021 | Bateman | A61F 2/2439 |
| 10,945,836 | B2* | 3/2021 | Braido | A61F 2/2418 |
| 10,952,847 | B2* | 3/2021 | Braido | A61F 2/966 |
| 10,973,633 | B2* | 4/2021 | Quijano | A61F 2/2445 |
| 11,147,666 | B2* | 10/2021 | Braido | A61F 2/2418 |
| 11,185,406 | B2* | 11/2021 | Haivatov | A61F 2/2412 |
| 11,197,755 | B1* | 12/2021 | Wallace | A61F 2/2436 |
| 11,357,624 | B2* | 6/2022 | Guyenot | A61F 2/2442 |
| 11,364,117 | B2* | 6/2022 | Dale | A61F 2/2418 |
| 11,510,777 | B1* | 11/2022 | Iyer | A61F 2/2427 |
| 11,517,430 | B1* | 12/2022 | Palmaz | A61L 27/34 |
| 11,589,981 | B2* | 2/2023 | Girard | A61F 2/2412 |
| 11,654,023 | B2* | 5/2023 | Zamani | A61F 2/2412 623/2.11 |
| 11,672,652 | B2* | 6/2023 | Buesseler | A61F 2/2412 623/2.18 |
| 11,844,691 | B2* | 12/2023 | Hammer | A61F 2/2418 |
| 11,850,148 | B2* | 12/2023 | Levi | A61F 2/2418 |
| 11,883,281 | B2* | 1/2024 | Hoang | A61F 2/2418 |
| 2001/0021872 | A1* | 9/2001 | Bailey | A61F 2/2469 623/2.18 |
| 2005/0283231 | A1 | 12/2005 | Haug et al. | |
| 2006/0178740 | A1* | 8/2006 | Stacchino | A61F 2/848 623/2.18 |
| 2007/0100435 | A1 | 5/2007 | Case et al. | |
| 2007/0142906 | A1* | 6/2007 | Figulla | A61F 2/2436 623/1.36 |
| 2008/0161911 | A1 | 7/2008 | Revuelta et al. | |
| 2008/0255661 | A1 | 10/2008 | Straubinger et al. | |
| 2009/0099653 | A1 | 4/2009 | Suri et al. | |
| 2009/0171447 | A1 | 7/2009 | Von Segesser et al. | |
| 2009/0216312 | A1 | 8/2009 | Straubinger et al. | |
| 2009/0222082 | A1 | 9/2009 | Lock et al. | |
| 2009/0240320 | A1 | 9/2009 | Tuval et al. | |
| 2009/0287296 | A1 | 11/2009 | Manasse | |
| 2009/0287299 | A1 | 11/2009 | Tabor et al. | |
| 2010/0161045 | A1 | 6/2010 | Righini et al. | |
| 2010/0204785 | A1* | 8/2010 | Alkhatib | A61F 2/2433 623/2.37 |
| 2010/0249923 | A1* | 9/2010 | Alkhatib | A61F 2/2409 623/2.18 |
| 2010/0298931 | A1 | 11/2010 | Quadri et al. | |
| 2011/0022157 | A1 | 1/2011 | Essinger et al. | |
| 2011/0098802 | A1* | 4/2011 | Braido | A61F 2/2466 623/2.11 |
| 2011/0137397 | A1* | 6/2011 | Chau | A61F 2/2412 623/2.37 |
| 2011/0178597 | A9 | 7/2011 | Navia et al. | |
| 2011/0208290 | A1 | 8/2011 | Straubinger et al. | |
| 2011/0245911 | A1 | 10/2011 | Quill et al. | |
| 2011/0313515 | A1 | 12/2011 | Quadri et al. | |
| 2011/0319989 | A1 | 12/2011 | Lane et al. | |
| 2012/0078353 | A1* | 3/2012 | Quadri | A61F 2/2436 623/2.14 |
| 2012/0158129 | A1 | 6/2012 | Duffy et al. | |
| 2012/0215303 | A1* | 8/2012 | Quadri | A61F 2/2427 623/2.18 |
| 2012/0271398 | A1 | 10/2012 | Essinger et al. | |
| 2013/0274873 | A1 | 10/2013 | Delaloye et al. | |
| 2013/0304200 | A1 | 11/2013 | McLean et al. | |
| 2014/0018915 | A1* | 1/2014 | Biadillah | A61F 2/2418 623/2.17 |
| 2014/0194981 | A1* | 7/2014 | Menk | A61F 2/2418 623/2.17 |
| 2014/0214157 | A1* | 7/2014 | Bortlein | A61F 2/243 623/2.11 |
| 2014/0222144 | A1* | 8/2014 | Eberhardt | A61F 2/2418 623/2.38 |
| 2014/0243966 | A1 | 8/2014 | Garde et al. | |
| 2014/0243969 | A1 | 8/2014 | Venkatasubramanian et al. | |
| 2014/0249622 | A1* | 9/2014 | Carmi | A61F 2/2418 623/2.11 |
| 2014/0277390 | A1 | 9/2014 | Ratz et al. | |
| 2014/0277417 | A1* | 9/2014 | Schraut | A61F 2/2418 623/2.17 |
| 2014/0277423 | A1* | 9/2014 | Alkhatib | A61F 2/2436 623/2.38 |
| 2014/0277426 | A1 | 9/2014 | Dakin et al. | |
| 2014/0277427 | A1* | 9/2014 | Ratz | A61F 2/2409 623/2.38 |
| 2014/0303719 | A1* | 10/2014 | Cox | A61F 2/2445 623/2.37 |
| 2014/0371844 | A1* | 12/2014 | Dale | A61F 2/2436 623/2.11 |
| 2015/0119974 | A1* | 4/2015 | Rothstein | A61F 2/2418 623/1.26 |

(56) References Cited

U.S. PATENT DOCUMENTS

| | | | |
|---|---|---|---|
| 2015/0142104 A1* | 5/2015 | Braido | A61F 2/2418 623/2.18 |
| 2015/0209136 A1 | 7/2015 | Braido et al. | |
| 2015/0305860 A1 | 10/2015 | Wang et al. | |
| 2015/0327995 A1* | 11/2015 | Morin | A61F 2/2436 623/2.17 |
| 2015/0351904 A1* | 12/2015 | Cooper | A61F 2/2418 623/2.1 |
| 2016/0030170 A1* | 2/2016 | Alkhatib | A61F 2/2418 623/2.17 |
| 2016/0030171 A1* | 2/2016 | Quijano | A61F 2/243 623/1.26 |
| 2016/0158007 A1* | 6/2016 | Centola | A61F 2/2418 623/2.11 |
| 2016/0235529 A1* | 8/2016 | Ma | A61F 2/2418 |
| 2016/0270910 A1* | 9/2016 | Birmingham | A61F 2/844 |
| 2016/0310267 A1* | 10/2016 | Zeng | A61F 2/2409 |
| 2016/0310268 A1* | 10/2016 | Oba | A61F 2/2433 |
| 2016/0331525 A1* | 11/2016 | Straubinger | A61F 2/2418 |
| 2016/0354201 A1 | 12/2016 | Keogh | |
| 2016/0361160 A1* | 12/2016 | Braido | A61F 2/2418 |
| 2016/0374802 A1 | 12/2016 | Levi et al. | |
| 2017/0056164 A1* | 3/2017 | Wang | A61F 2/2415 |
| 2017/0056169 A1* | 3/2017 | Johnson | A61F 2/2433 |
| 2017/0056215 A1* | 3/2017 | Nagesh | A61F 2/856 |
| 2017/0065418 A1* | 3/2017 | Skarsgard | A61F 2/2487 |
| 2017/0071734 A1* | 3/2017 | Delaloye | A61F 2/2418 |
| 2017/0079786 A1* | 3/2017 | Li | A61F 2/2418 |
| 2017/0086971 A1* | 3/2017 | Braido | A61F 2/2418 |
| 2017/0165053 A1* | 6/2017 | Buesseler | A61F 2/2412 |
| 2017/0189180 A1 | 7/2017 | Alkhatib | |
| 2017/0189181 A1 | 7/2017 | Alkhatib et al. | |
| 2017/0209261 A1 | 7/2017 | Bortlein et al. | |
| 2017/0252154 A1 | 9/2017 | Tubishevitz et al. | |
| 2017/0290661 A1 | 10/2017 | Von Segesser et al. | |
| 2017/0325945 A1* | 11/2017 | Dale | A61F 2/2412 |
| 2017/0340438 A1 | 11/2017 | Salahieh et al. | |
| 2018/0116798 A1* | 5/2018 | Perszyk | A61F 2/2445 |
| 2018/0256327 A1* | 9/2018 | Perszyk | A61F 2/2436 |
| 2019/0000619 A1* | 1/2019 | Quijano | A61F 2/2436 |
| 2019/0046316 A1* | 2/2019 | Chen | A61F 2/2418 |
| 2019/0099265 A1* | 4/2019 | Braido | A61F 2/86 |
| 2019/0183639 A1* | 6/2019 | Moore | A61F 2/2409 |
| 2019/0274832 A1* | 9/2019 | Delaloye | A61F 2/2418 |
| 2020/0078167 A1* | 3/2020 | Quijano | A61F 2/2418 |
| 2021/0052379 A1* | 2/2021 | Zhao | A61F 2/2409 |
| 2021/0275300 A1* | 9/2021 | Walsh | A61F 2/2439 |
| 2021/0322155 A1* | 10/2021 | McVeigh | A61F 2/2418 |
| 2021/0346153 A1* | 11/2021 | Vietmeier | A61F 2/2436 |
| 2022/0168097 A1* | 6/2022 | Levi | A61F 2/2418 |
| 2022/0183831 A1* | 6/2022 | Burkart | A61F 2/2418 |
| 2022/0192823 A1* | 6/2022 | Darekar | A61F 2/2418 |
| 2022/0192824 A1* | 6/2022 | Vidlund | A61F 2/2418 |
| 2022/0233309 A1* | 7/2022 | Yoganathan | A61F 2/2418 |
| 2022/0257374 A1* | 8/2022 | Agreli | A61F 2/2418 |
| 2022/0265445 A1* | 8/2022 | Bukin | A61F 2/2415 |
| 2022/0313428 A1* | 10/2022 | Bergin | A61F 2/2418 |
| 2022/0338979 A1* | 10/2022 | Benichou | A61F 2/2409 |
| 2023/0038102 A1* | 2/2023 | Hayes | A61F 2/2418 |
| 2023/0038809 A1* | 2/2023 | Clapp | A61F 2/2418 |
| 2023/0040369 A1* | 2/2023 | Ma | A61F 2/2418 |
| 2023/0118855 A1* | 4/2023 | Gifford, III | A61F 2/2418 623/1.11 |
| 2023/0149162 A1* | 5/2023 | Gurovich | A61F 2/2418 623/2.17 |
| 2023/0210658 A1* | 7/2023 | Syed | A61F 2/2433 623/2.11 |

FOREIGN PATENT DOCUMENTS

| | | |
|---|---|---|
| WO | 2013106585 A1 | 7/2013 |
| WO | 2014139545 A1 | 9/2014 |

\* cited by examiner

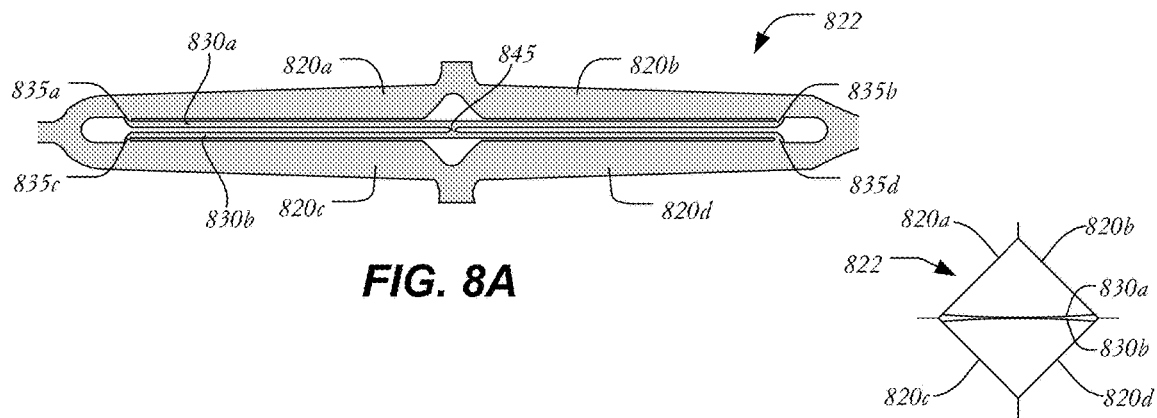
FIG. 8A
FIG. 8B
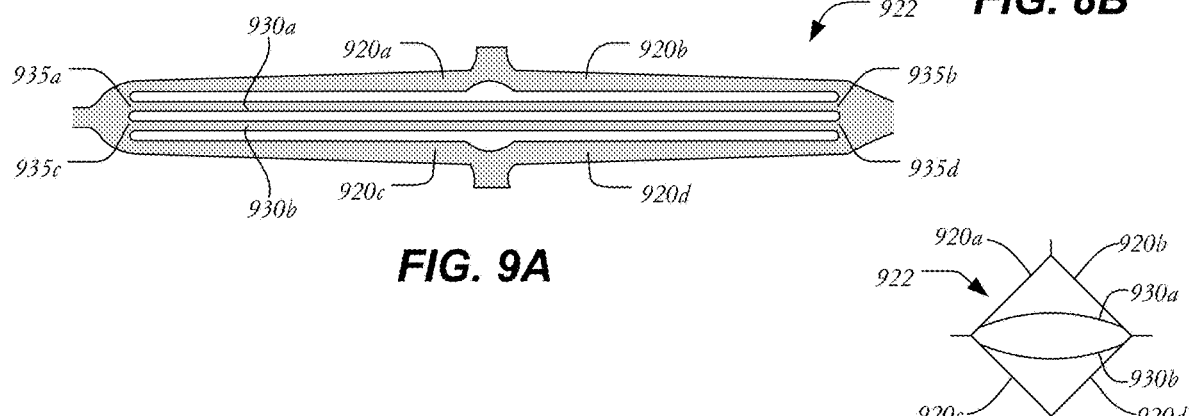
FIG. 9A
FIG. 9B
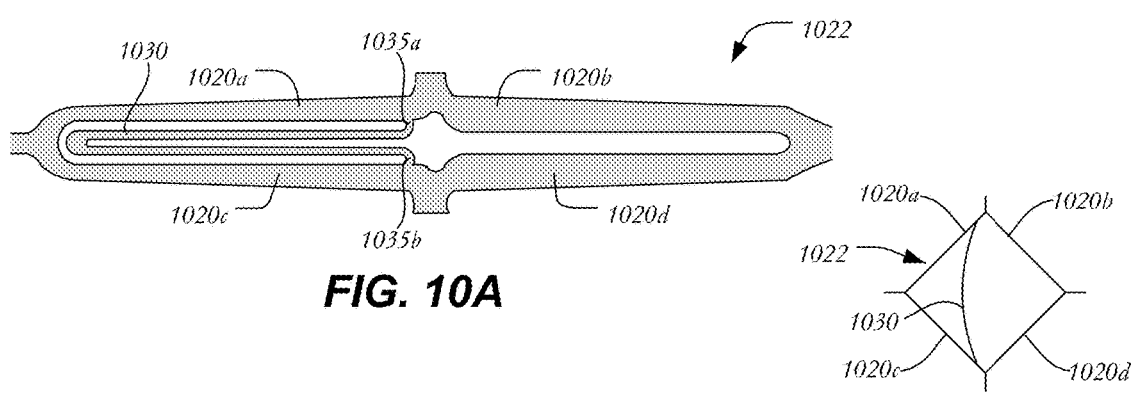
FIG. 10A
FIG. 10B

BOWED RUNNERS AND CORRESPONDING VALVE ASSEMBLIES FOR PARAVALVULAR LEAK PROTECTION

CROSS-REFERENCE TO RELATED APPLICATIONS

The present application is a continuation of U.S. patent application Ser. No. 16/299,969 filed Mar. 12, 2019, which is a continuation of U.S. patent application Ser. No. 15/921,106, filed Mar. 14, 2018 (now U.S. Pat. No. 10,271,946), which is a continuation of U.S. patent application Ser. No. 15/118,991 (now U.S. Pat. No. 9,949,825), filed Aug. 15, 2016, which is a national phase entry under 35 U.S.C. § 371 of International Application No. PCT/US2015/015533 filed Feb. 12, 2015, published in English, which claims priority from U.S. Provisional Patent Application No. 61/941,012, filed Feb. 18, 2014, the disclosures of which are incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a stent extending between a proximal end and a distal end and including a plurality of struts forming cells, the stent having a collapsed condition and an expanded condition. At least one runner is coupled to a cell, the at least one runner being configured to transition from a first configuration to a second configuration when the stent moves from the collapsed condition to the expanded condition, the at least one runner projecting radially outwardly from the cell in the second configuration. A valve assembly is disposed within the stent, the valve assembly including a plurality of leaflets, a cuff at least partially disposed on a luminal surface of the stent and a covering material disposed on an abluminal surface of the stent and covering the at least one runner in the second configuration.

In some embodiments, a prosthetic heart valve for replacing a native valve includes a stent extending between a proximal end and a distal end and including a plurality of struts forming cells and a plurality of runners, the stent having a collapsed condition and an expanded condition, the struts defining a first diameter and the runners defining a second diameter, the second diameter being greater than the first diameter. A valve assembly is disposed within the stent, the valve assembly including a plurality of leaflets and a cuff at least partially disposed on a luminal surface of the stent and partially disposed on an abluminal surface of the stent to cover the runner.

BRIEF DESCRIPTION OF THE DRAWINGS

Various embodiments in accordance with the present disclosure will now be described with reference to the appended drawings. It is to be appreciated that these drawings depict only some embodiments and are therefore not to be considered limiting of its scope.

FIGS. 5A-10B are enlarged highly schematic partial side views of several variations of collapsed stent cells having runners and their respective shapes in the bowed configuration;

DETAILED DESCRIPTION

Despite various improvements that have been made to the collapsible prosthetic heart valve delivery process, conventional devices suffer from some shortcomings. For example, with conventional self-expanding valves, the clinical success of the valve is dependent on accurate deployment and anchoring. Inaccurate deployment and anchoring of the valve increases risks, such as those associated with valve migration, which may cause complications due to the obstruction of the left ventricular outflow tract. Inaccurate deployment and anchoring may also result in the leakage of blood between the implanted heart valve and the native valve annulus, commonly referred to as paravalvular leakage (also known as "perivalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient or performing an additional valve-in-valve procedure. Removing a fully deployed heart valve increases the length of the procedure as well as risks. Thus, methods and devices are desirable that would reduce the need to remove a prosthetic heart valve from a patient. Methods and devices are also desirable that would reduce the likelihood of paravalvular leakage due to gaps between the implanted heart valve and patient tissue.

There therefore is a need for further improvements to the devices, systems, and methods for positioning and sealing collapsible prosthetic heart valves. Specifically, there is a need for further improvements to the devices, systems, and methods for accurately implanting a prosthetic heart valve. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

Figure 1:
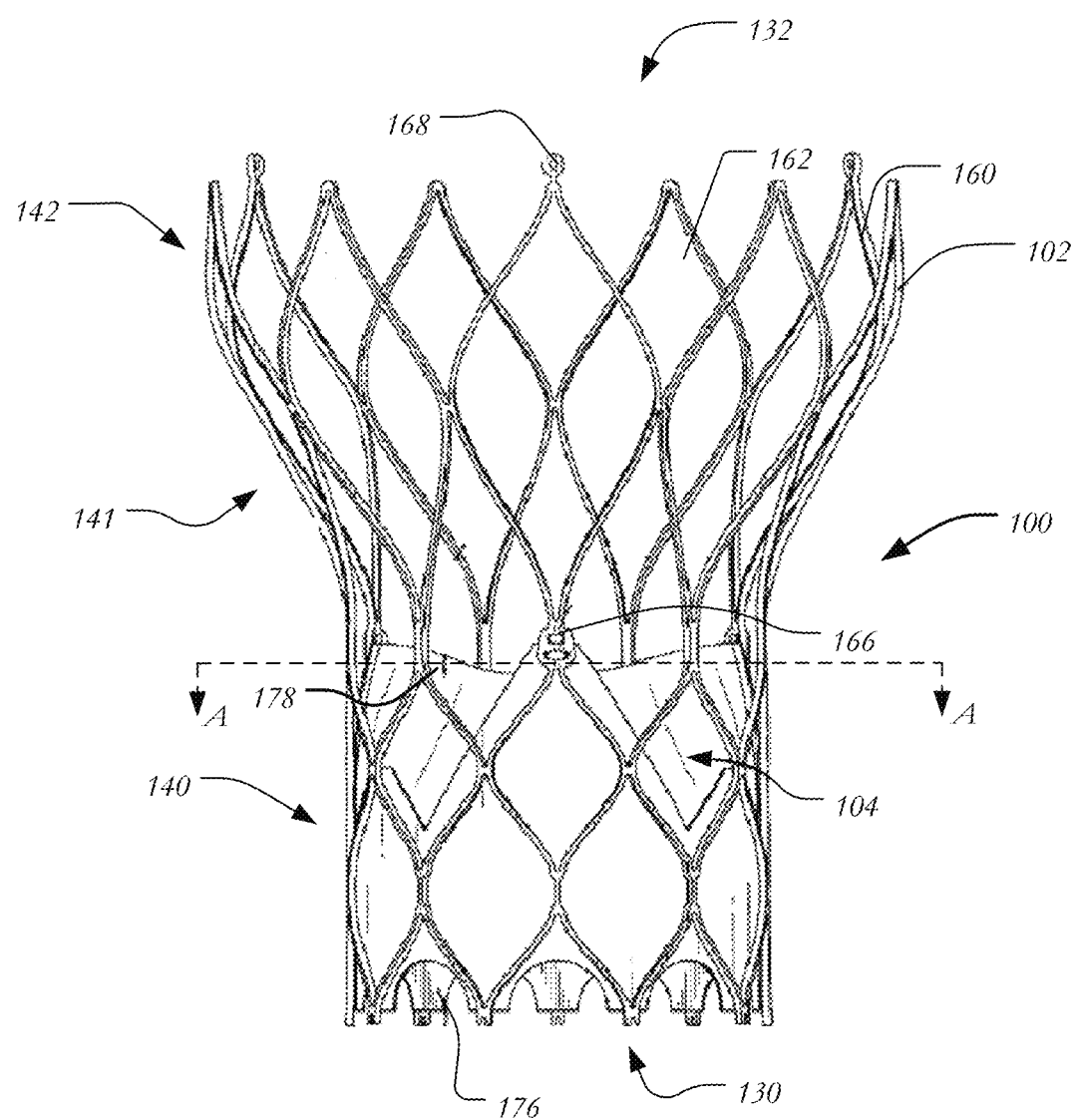
FIG. 1 is a side elevational view of a conventional prosthetic heart valve.

The sealing portions of the present disclosure may be used in connection with collapsible prosthetic heart valves. FIG. 1 shows one such collapsible stent-supported prosthetic heart valve 100 including a stent 102 and a valve assembly 104 as is known in the art. Prosthetic heart valve 100 is designed to replace a native tricuspid valve of a patient, such as a native aortic valve. It should be noted that while the disclosures herein relate predominantly to prosthetic aortic valves having a stent with a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141 and aortic section 142 adjacent distal end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, Polyethylene terephthalate (PET), ultra-high-molecular-weight polyethylene (UHMWPE), or polytetrafluoroethylene (PTFE).

Leaflets 178 may be attached along their belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed configuration. The delivery device may be introduced into a patient using a transfemoral, transaortic, transsubclavian, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
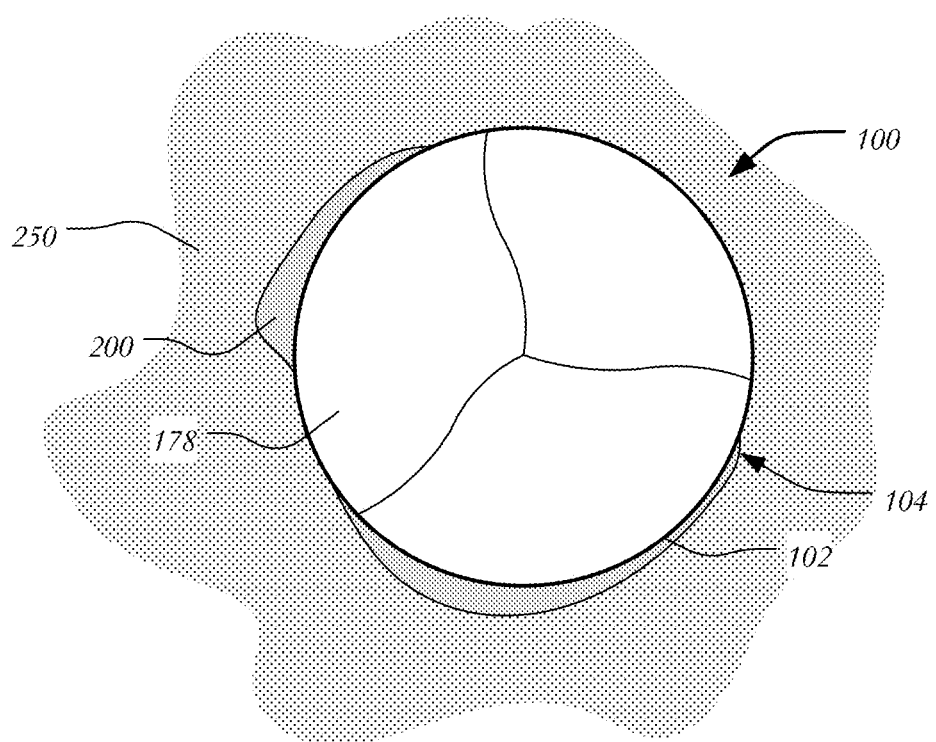
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance Such improper fitment may be due to suboptimal native valve annulus geometry due, for example, to calcification of native valve annulus 250 or to unresected native leaflets.

Figure 3A:
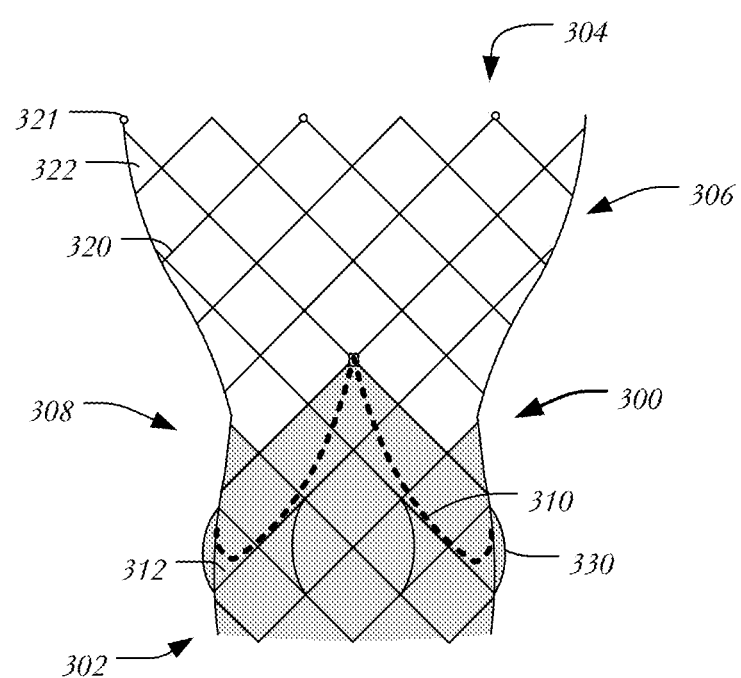
FIG. 3A is a highly schematic side view of one embodiment of a heart valve having bowed runners intended to fill irregularities between the heart valve and the native valve annulus.

FIG. 3A illustrates one embodiment of heart valve 300 intended to fill the irregularities between the heart valve and native valve annulus 250 shown in FIG. 2. Heart valve 300 extends between proximal end 302 and distal end 304, and may generally include stent 306 and valve assembly 308 having a plurality of leaflets 310 and cuff 312. Heart valve 300 may be formed of any of the materials and in any of the configurations described above with reference to FIG. 1.

Stent 306 may include a plurality of struts 320. Certain struts 320 may terminate in retaining elements 321 at distal end 304. Struts 320 may come together to form cells 322 connected to one another in one or more annular rows around the stent. Connected to struts 320 are a plurality of runners 330, which are additional struts that bow or bulge out radially when stent 306 is expanded, as will be described in greater detail with reference to FIGS. 3B and 3C.

Figure 3B:
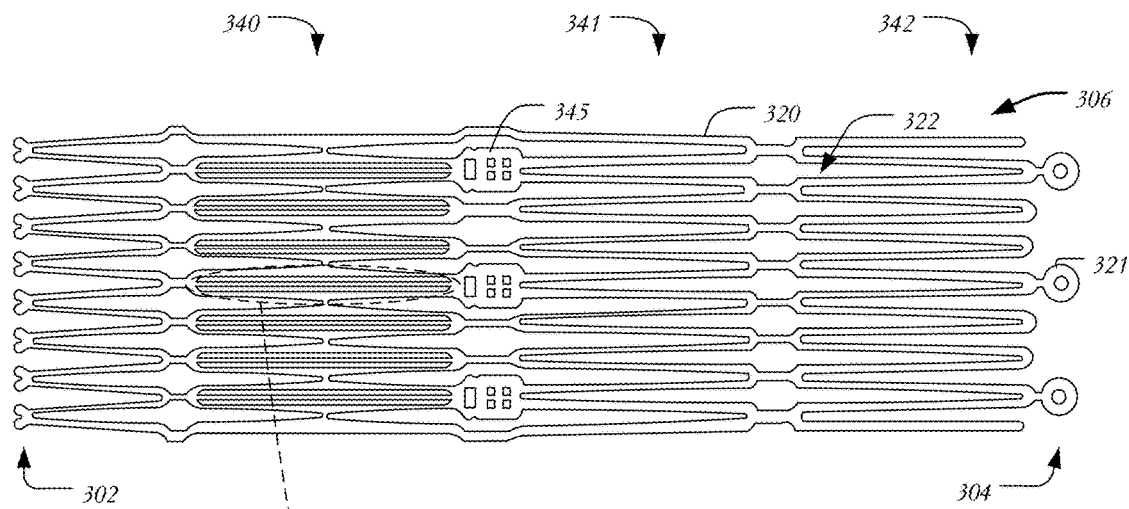
FIG. 3B is a developed view of the stent of the heart valve of FIG. 3A in the collapsed configuration.

In order to better appreciate the attachment and placement of runners 330, stent 306 is shown in FIG. 3B in its collapsed configuration. For the sake of clarity, valve assembly 308 is not shown in this figure. In the collapsed configuration of stent 306, each of cells 322 is also collapsed. Stent 306 extends from proximal or annulus end 302 of heart valve 300 to distal or aortic end 304, and includes annulus section 340 adjacent proximal end 302, aortic section 342 adjacent distal end 304, and transition section 341 between annulus section 340 and aortic section 342. Commissure features 345 may be positioned entirely within annulus section 340 or at the juncture of annulus section 340 and transition section 341 as shown.

Figure 3C:
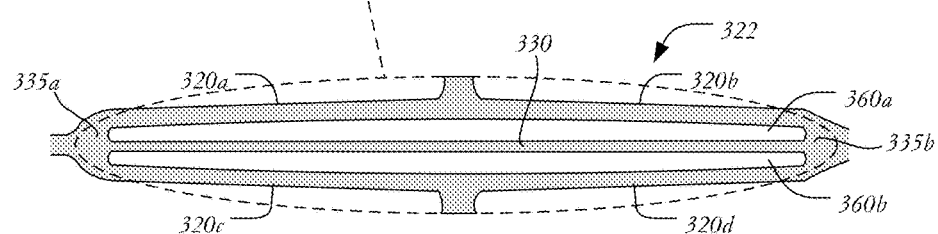
FIGS. 3C and 3D are enlarged highly schematic partial views of a stent cell having a runner in the collapsed configuration and bowed configuration, respectively.
Figure 3D:
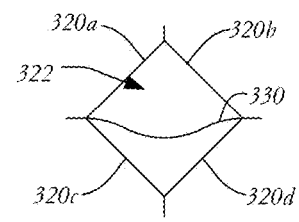

One or more cells 322 may include runners 330. An enlarged partial side view of cell 322 including a runner 330 is shown in FIG. 3C. Four struts 320a, 320b, 320c, 320d may join to form cell 322, each strut being attached to two adjacent struts. In the collapsed configuration of stent 306, cell 322 may be stadium-shaped as shown. In the expanded configuration of stent 306, cell 322 may shorten in the length direction of stent 306 between proximal end 302 and distal end 304, and struts 320 may generally form a diamond shape (FIG. 3D).

Runners 330 may extend from first attachment end 335a where struts 320a and 320c meet to second attachment end 335b where struts 320b and 320d meet, and may be affixed to stent 306 by welding, adhesive, or any other suitable technique known in the art. Moreover, instead of being separately formed and affixed to stent 306 at attachment ends 335a,335b, runners 330 may be integrally formed with stent 306, such as by laser cutting both stent 306 and runners 330 from the same tube. Additionally, runners 330 may be formed of a shape memory material such as those described above for forming stent 102 of FIG. 1, and may have a substantially linear configuration in the collapsed configuration of heart valve 300 (FIG. 3C) and a curved or bowed configuration in the expanded configuration of heart valve 300 (FIG. 3D).

In the collapsed configuration, runner 330 may bisect cell 322 into first portion 360a and second portion 360b. As the length of cell 322 shortens in the expanded configuration of heart valve 300, the unchanged length of runner 330 causes the runner to bow or deflect outwardly of the curved surface defined by struts 320a, 320b, 320c, 320d. Stent 306 may also be heat set such that struts 320 and runner 330 return to a predetermined shape in the fully expanded configuration (e.g., when no external forces are applied thereto). When cuff 312 (FIG. 3A) is coupled to the abluminal surface of annulus section 340 of stent 306, the cuff is substantially tubular when runners 330 are not bowed outwardly. When runners 330 bow outwardly on the expansion of heart valve 300, they form protuberances in cuff 312 to help seal heart valve 300 within the native valve annulus.

Figure 4A:
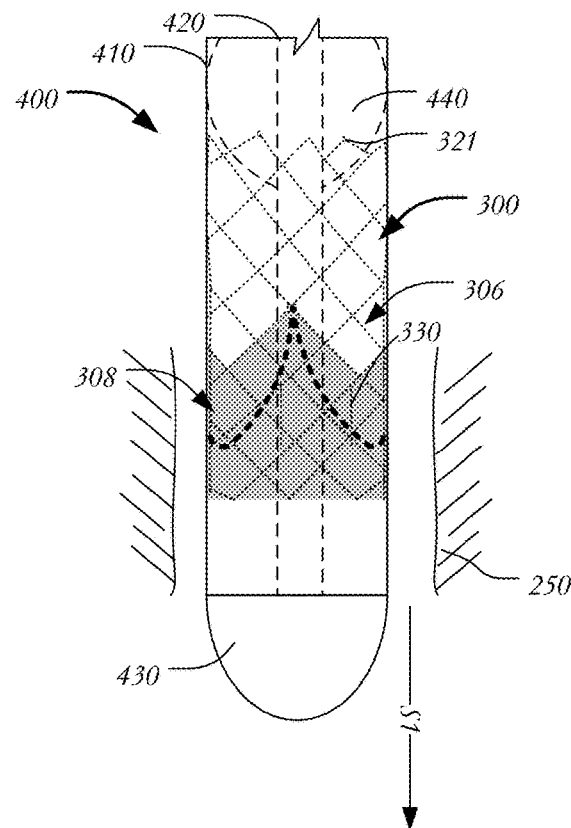
FIGS. 4A-D are highly schematic side views of one method of delivering and deploying the heart valve of FIG. 3A within the native valve annulus.

A method of delivering and implanting heart valve 300 will now be described with reference to FIGS. 4A-D. A delivery system 400 may be used to deliver and deploy heart valve 300 in native valve annulus 250, and may generally include sheath 410, shaft 420, atraumatic tip 430 and hub 440. Sheath 410 may be slidable relative to shaft 420. Heart valve 300, including stent 306, valve assembly 308 and runners 330, may be disposed within sheath 410 about shaft 420 (FIG. 4A). Hub 440 may be coupled to shaft 420 and configured to mate with retaining elements 321 of heart valve 300. Runners 330 of heart valve 300 may be disposed in the linear configuration of FIG. 3C, substantially parallel to sheath 410, during delivery. Specifically, though runners 330 are configured to return to their curved configuration, they may be kept substantially linear by being constrained within sheath 410. By doing so, heart valve 300 may be delivered to the native valve annulus using delivery system 400 without increasing the radius of sheath 410, avoiding the need to increase the crimp profile of the heart valve within delivery system 400. A large delivery system may be incapable of being passed through the patient's vasculature, while a delivery system having a heart valve with a smaller crimp profile may be easier to navigate through a patient's body and may also reduce the length of the implantation procedure. In the example shown in FIGS. 4A-D, delivery system 400 is delivered from the aorta toward the left ventricle as indicated by arrow 51. If heart valve 300 or delivery system 400 includes echogenic materials, such materials may be used to guide delivery system 400 to the appropriate position using the assistance of three-dimensional echocardiography to visualize heart valve 300 within the patient. Alternative visualization techniques known in the art are also contemplated herein.

Figure 4B:
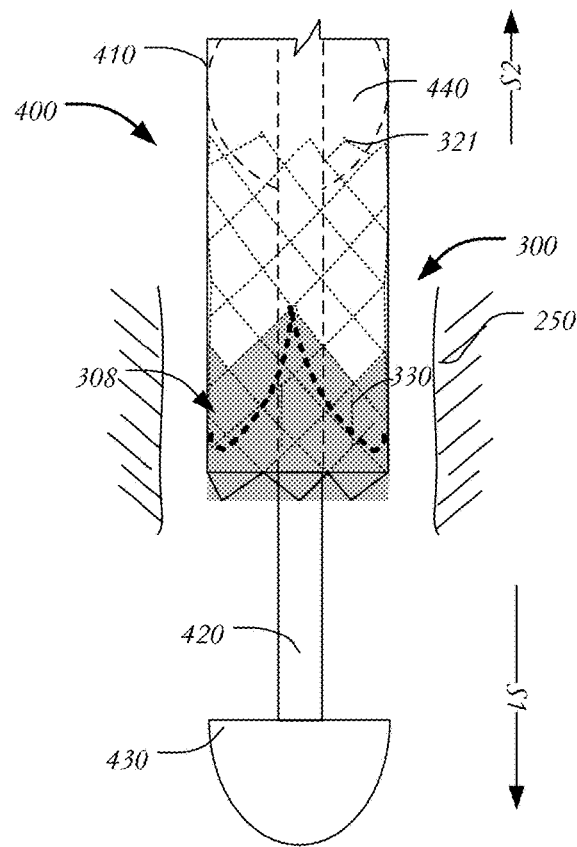
Figures 4C, 4D:
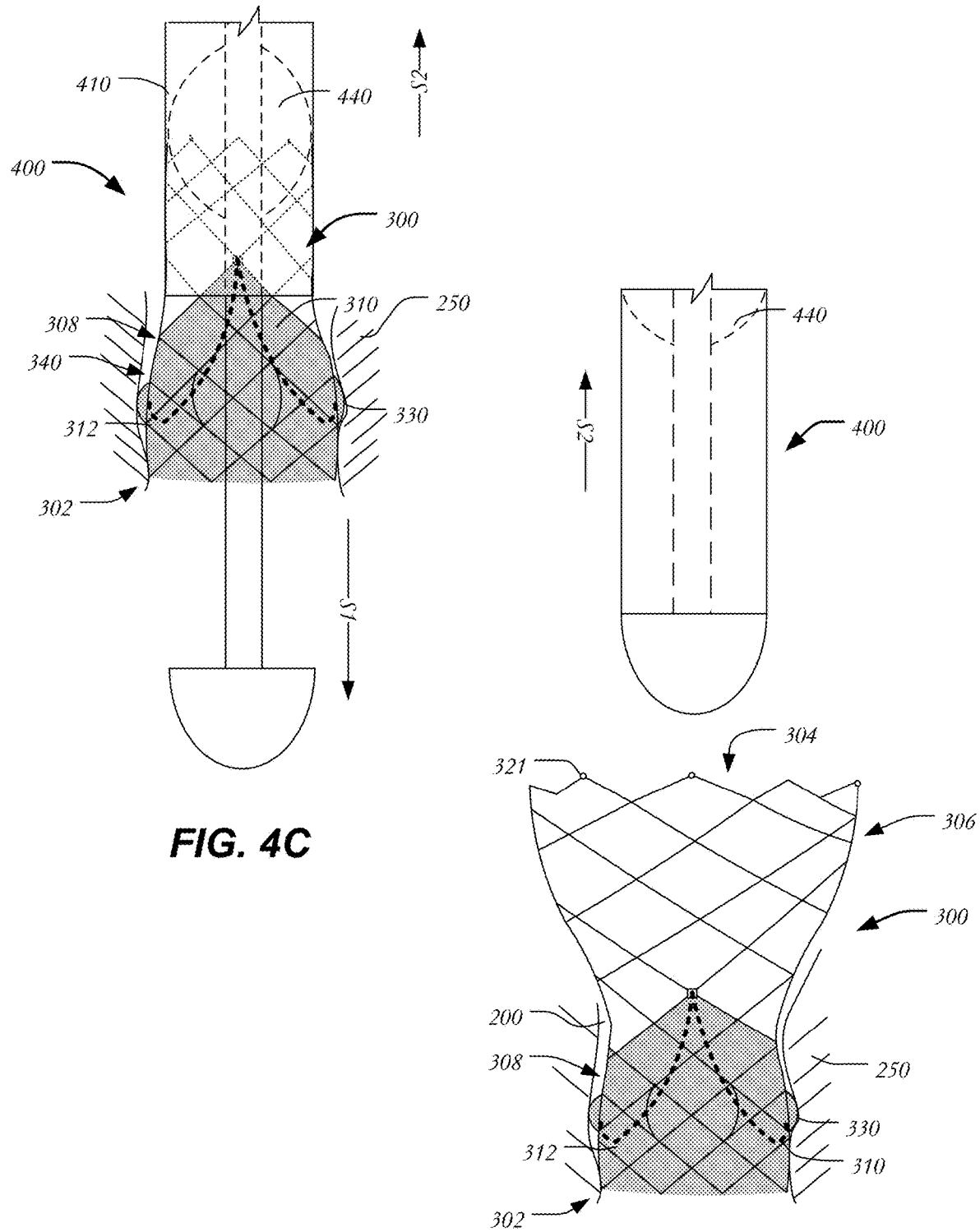

When delivery system 400 has reached the proper location (e.g., atraumatic tip 430 is just past native valve annulus 250), atraumatic tip 430 may be advanced slightly in the direction of arrow 51 toward the left ventricle by pushing shaft 420 toward atraumatic tip 430 while holding sheath 410 in place, which serves to decouple atraumatic tip 430 from sheath 410 (FIG. 4B). Sheath 410 may then be retracted in the direction of arrow S2 toward the aorta. With sheath 410 slightly retracted, heart valve 300 begins to emerge from the sheath. As sheath 410 is further retracted in the direction of arrow S2, more of heart valve 300 is exposed until annulus section 340 is fully exposed and runners 330 become bowed (FIG. 4C). Thus, sheath 410 may be retracted until heart valve 300 is free to self-expand within native valve annulus 250. While heart valve 300 is partially deployed (e.g., a portion of heart valve 300 is outside sheath 410, but heart valve 300 is not fully detached from delivery system 400), if it appears that heart valve 300 needs to be recaptured and redeployed due to, for example, improper positioning or orientation, sheath 410 may be slid over shaft 420 in the direction of arrow 51 to recapture heart valve 300 within sheath 410. During recapture, sheath 410 may push against bowed runners 330 to straighten them to the linear configuration shown in FIG. 3C. This process may be repeated until heart valve 300 is properly positioned and deployed within native valve annulus 250.

After sheath 410 has been fully retracted to expose heart valve 300, runners 330, now in their bowed or curved configuration, push cuff 312 outwardly against native valve annulus 250 and occlude gaps 200 between heart valve 300 and native valve annulus 250, thereby reducing or eliminating the amount of blood that passes around heart valve 300 through gaps 200 (FIG. 4D). Retaining elements 321 of heart valve 300 may decouple from hub 440 as heart valve 300 fully expands, atraumatic tip 430 may be retracted through heart valve 300 in the direction of arrow S2 and delivery system 400 may be removed from the patient.

Several variations of runners are described with reference to FIGS. 5A-10B. In each variation, a collapsed cell is shown along with a schematic of the cell in the expanded configuration. As used herein the terms expanded and collapsed may refer to the configurations of a cell, a stent, a heart valve and a valve assembly interchangeably.

Figure 5A:
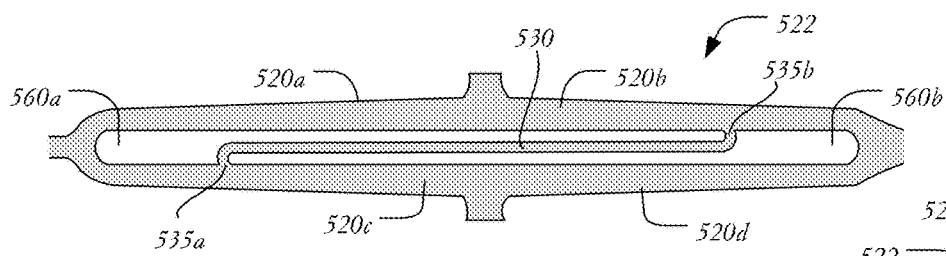
Figure 5B:
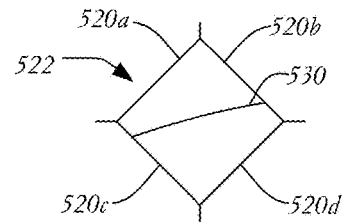

FIG. 5A shows cell 522 of a stent having four struts 520a, 520b, 520c, 520d, each strut being attached to two adjacent struts. In the collapsed configuration of the stent, cell 522 may be stadium-shaped as shown (FIG. 5A). Runner 530 may extend between two attachment ends 535a, 535b. Specifically, runner 530 may be joined to third strut 520c at first attachment end 535a and to diagonally-opposed second strut 520b at second attachment end 535b. Runner 530 may diagonally divide cell 522 substantially equally into first portion 560a and second portion 560b in the collapsed configuration. When cell 522 is placed in the expanded configuration (FIG. 5B), the cell may form a substantially diamond shape, with runner 530 stretching diagonally from strut second 520b to third strut 520c across the cell. Because attachment ends 535a,535b are closer to one another in the expanded configuration than in the collapsed configuration, runner 530 may bow outwardly to form a protuberance.

Figure 6A:
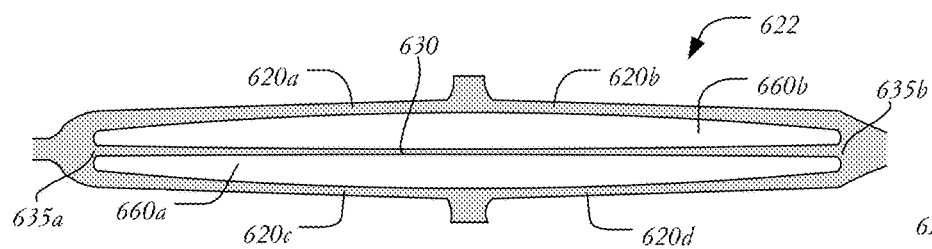
Figure 6B:
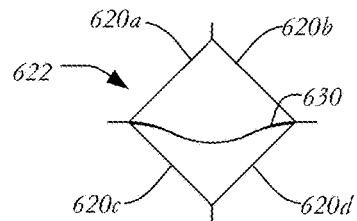

FIG. 6A shows cell 622 of a stent having four struts 620a, 620b, 620c, 620d, each strut being attached to two adjacent struts. Runner 630 may extend between two attachment ends 635a, 635b located at junctions of two struts (e.g., attachment end 635a is at the junction of struts 620a and 620c, while attachment end 635b is at the junction of struts 620b and 620d) and bisect cell 622 into substantially equal first portion 660a and second portion 660b in the collapsed configuration. Runner 630 may be tapered as shown, having a larger width at attachment ends 635a, 635b than at its middle. A tapered runner 630 may provide added flexibility and may be easier to heat set so that it readily returns to the bowed configuration when cell 622 is expanded, as shown in FIG. 6B.

Figure 7A:
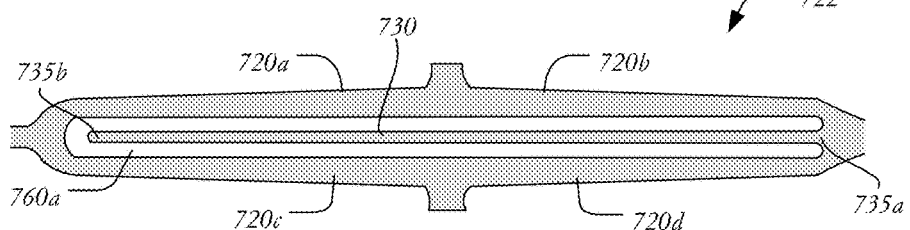
Figure 7B:
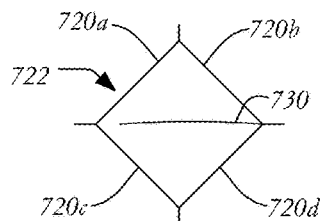

FIG. 7A shows cell 722 of a stent having four struts 720a, 720b, 720c, 720d, each strut being attached to two adjacent struts. Unlike cell 322, runner 730 is joined to cell 722 at a single attachment end 735a only and is able to deflect at free end 735b opposite attachment end 735a. It will be understood that the single point of attachment may be disposed at any of struts 720a, 720b, 720c, 720d or at the intersection of any two struts (e.g., at the intersection of second strut 720b and fourth strut 720d as shown, or at the opposite end at the intersection of first strut 720a and third strut 720c, or at the intersection of first strut 720a and second strut 720b, or third strut 720c and fourth strut 720d). In the collapsed configuration, runner 730 fills a portion of cell 722 so that a U-shaped cutout 760a is formed within cell 722. In the expanded configuration (FIG. 7B), runner 730 is capable of bowing radially outwardly to provide paravalvular sealing.

FIG. 8A shows cell 822 of a stent having four struts 820a, 820b, 820c, 820d, each strut being attached to two adjacent struts. Cell 822 includes a pair of runners 830a, 830b that are substantially parallel to one another in the collapsed configuration. First runner 830a is coupled to first strut 820a at first attachment end 835a and to second strut 820b at second attachment end 835b, while second runner 830b is coupled to third strut 820c at third attachment end 835c and to fourth strut 820d at fourth attachment end 835d. Moreover, first and second runners 830a, 830b are coupled to one another at midpoint 845, which keeps runners 830a, 830b close together along a midline of the diamond shaped cell 822 in the expanded configuration (FIG. 8B). Twin runners 830a, 830b may provide a larger support surface over which a cuff may be stretched to better seal a heart valve within a native valve annulus.

FIG. 9A shows another variation having twin runners. Cell 922 includes four struts 920a, 920b, 920c, 920d, each strut being attached to two adjacent struts. Cell 922 includes a pair of runners 930a, 930b that are substantially parallel to one another in a collapsed configuration. First runner 930a is coupled to the junction of first strut 920a and third strut 920c at first attachment end 935a and to the junction of second strut 920b and third strut 920d at second attachment end 935b, while second runner 930b is coupled to the same two junctions at third attachment end 935c and fourth attachment end 935d. Runners 930a, 930b are not joined to one another except for having attachment ends near one another. When cell 922 expands, runners 930a, 930b bow outwardly and separate to provide scaffolding upon which a cuff may be stretched (FIG. 9B). Instead of the cuff being stretched out over a single bowed runner or dual bowed runners attached at a midpoint, stretching the cuff over twin bowed runners that are spaced apart from one another provides a greater support area. Thus, this separation of bowed runners 930*a*, 930*b* may provide a more uniform protuberance for better sealing of a heart valve within the native valve annulus.

Another variation, shown in FIG. 10A, includes cell 1022 having four struts 1020*a*, 1020*b*, 1020*c*, 1020*d*, each strut being attached to two adjacent struts. Runner 1030 is formed as a U-shaped nested strut in the collapsed configuration, being attached to two adjacent struts 1020*a*, 1020*c* at attachment ends 1035*a*, 1035*b*, respectively. In the expanded configuration, runner 1030 bows radially outwardly to form a protuberance (FIG. 10B). Because bowed runner 1030 is attached to adjacent struts 1020*a*, 1020*c* in the same half of cell 1022 and stretches between two attachment points at about the same longitudinal position, in the expanded configuration, bowed runner 1030 extends laterally across cell 1022.

Additionally, runners may be provided at a variety of locations on a stent. For example, in FIG. 11A heart valve 1100A extends between proximal end 1102 and distal end 1104, and may generally include stent 1106 and valve assembly 1108 having a plurality of leaflets 1110 and cuff 1112. Heart valve 1100A may be formed of any of the materials and in any of the configurations described above with reference to FIG. 1.

Figure 11A:
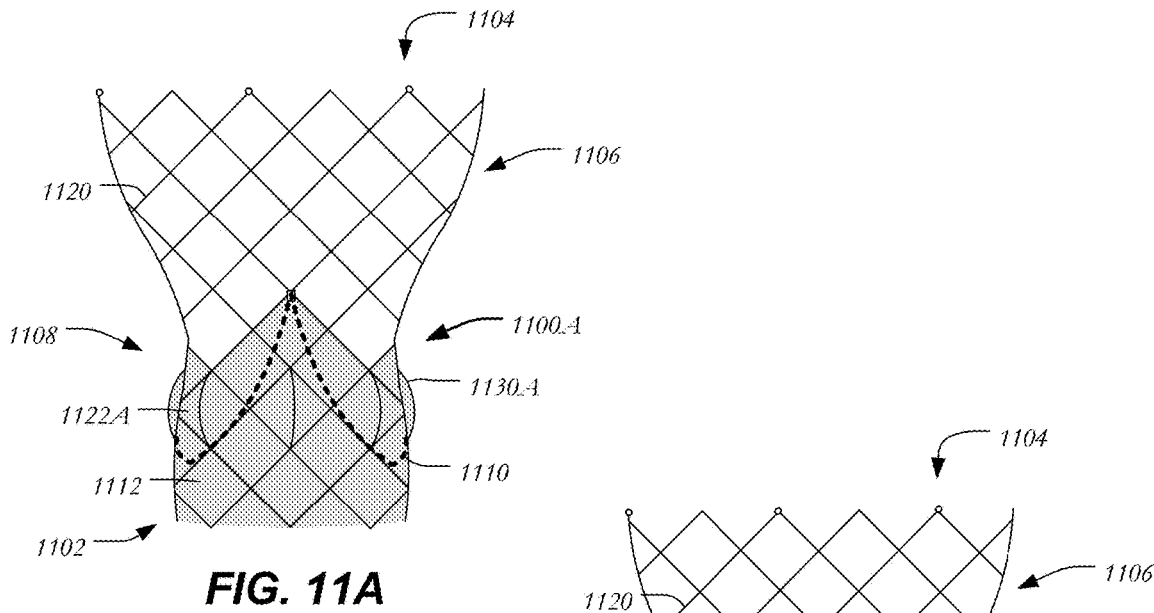
FIGS. 11A-C are enlarged highly schematic side views of heart valves having bowed runners at various longitudinal positions.
Figure 11B:
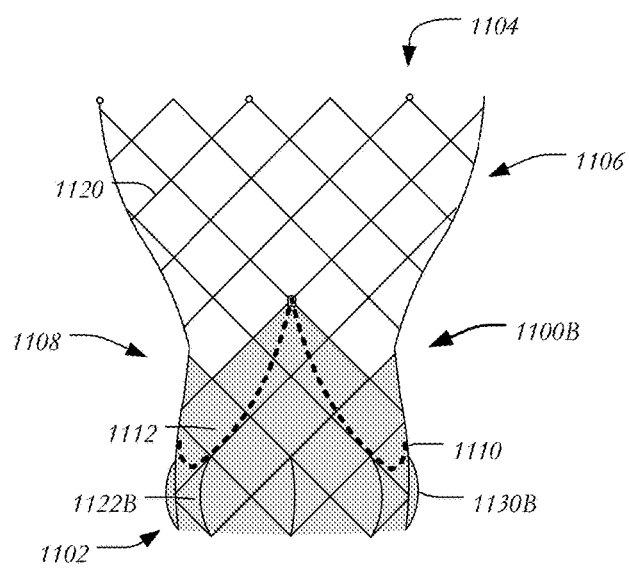
Figure 11C:
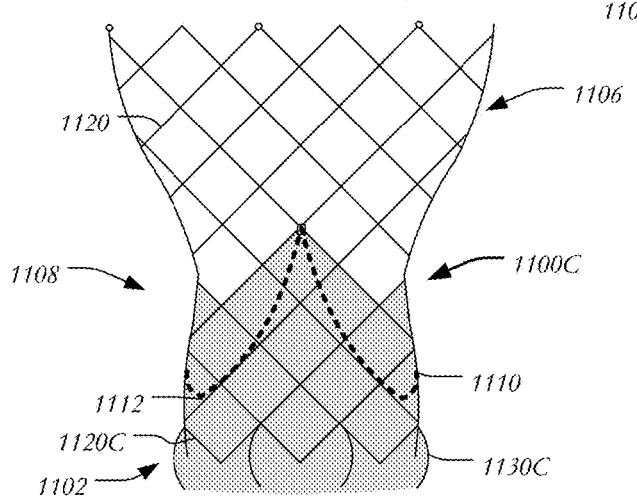

Stent 1106 may include a plurality of struts 1120, which may come together to form cells such as cell 1122A connected to one another in one or more annular rows around the stent. Connected to struts 1120 are a plurality of runners 1130A, which are additional struts that bow or bulge out radially when stent 1106 is expanded, as will be described in greater detail with reference to FIGS. 11B and 11C. As shown in FIG. 11A, runners 1130A are attached to the third full row of cells 1122A from proximal end 1102 so that at least a portion of each runner is disposed radially outward of leaflets 1110. In a second variation, shown in FIG. 11B, heart valve 1100B includes runners 1130B attached to the first full row of cells 1122B from proximal end 1102. In yet another variation, shown in FIG. 11C, heart valve 1100C includes runners 1130C attached to the bottom-most struts 1120C so that they extend proximally of the proximal end 1102 of stent 1106. It will be understood that the longitudinal position of runners 1130 may be varied anywhere within the annulus section and/or transition section. Additionally, multiple rows of runners may be disposed on stent 1106. Moreover, each cell in an annular row of cells need not include a runner. Thus, there may be more runners in one annular row of cells than in another annular row of cells.

Figure 12:
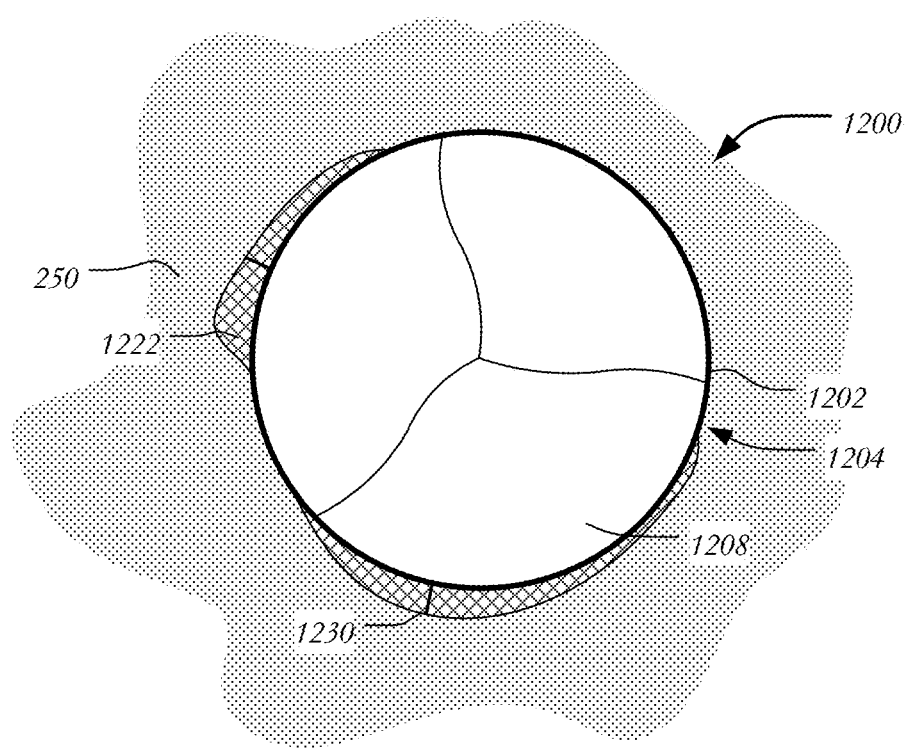
FIG. 12 is a highly schematic cross-sectional view of a heart valve having bowed runners disposed within a native valve annulus.

FIG. 12 is a highly schematic cross-sectional view showing heart valve 1200 having stent 1202, valve assembly 1204 including leaflets 1208 and a cuff 1222, and bowed runners 1230 supporting portions of cuff 1222. As seen in FIG. 12, bowed runners 1230 extend radially outward from stent 1202 to press cuff 1222 into the gaps between heart valve 1200 and native valve annulus 250. Cuff 1222 may be capable of promoting tissue growth between heart valve 1200 and native valve annulus 250. For example, cuff 1222 may be innately capable or promoting tissue growth and/or may be treated with a biological or chemical agent to promote tissue growth, further enabling it to seal the heart valve within the native valve annulus. When runners 1230 are functioning properly, heart valve 1200 will be adequately sealed within native valve annulus 250 so that blood flows through leaflets 1208 of valve assembly 1204, and so that blood flow through any gaps formed between heart valve 1200 and native valve annulus 250 is limited or reduced.

The preceding embodiments have illustrated a simplified arrangement in which a cuff is disposed on the abluminal surface of a stent and attached to runners such that the expansion of the runners pushes the cuff outwardly toward walls of the native valve annulus. Other configurations of the cuff are also possible as illustrated below.

Figure 13:
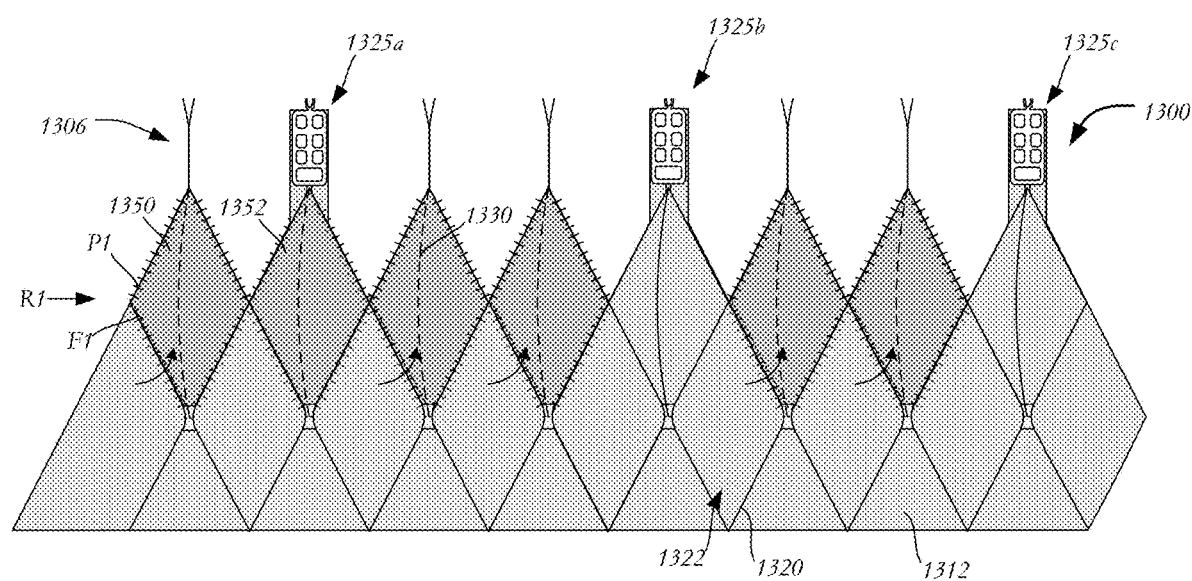
FIGS. 13-15 are highly schematic developed views of portions of heart valves including cuffs having folding flaps for covering runners in a first row.

FIG. 13 is a schematic developed view of a portion of heart valve 1300 including stent 1306 with cuff 1312 attached to same. For the sake of clarity, leaflets of the valve assembly are not shown. Stent 1306 includes a plurality of struts 1320 attached together to form diamond-shaped cells 1322 as has been described above. Three commissure features 1325*a*, 1325*b*, 1325*c* are also shown attached to struts 1320. Runners 1330 are formed in each of cells 1322 in row R1 located directly below commissure features 1325.

Cuff 1312 is disposed on the luminal surface of stent 1306 (i.e., FIG. 13 is a schematic illustration of the exterior of heart valve 1300). Cuff 1312 may be formed of a polymer, a fabric or tissue, such as bovine, porcine, ovine, equine, kangaroo, PTFE, UHMWPE, PET, Dacron, PVA, Polyurethane, silicone or combinations thereof. Cuff 1312 includes diamond-shaped flaps 1350 for folding over certain cells 1322 in row R1 that include runners 1330. Each flap 1350 may be attached to cuff 1312 or formed integrally with cuff 1312 and may be folded at fold line F1 from the luminal surface of stent 1306 to the abluminal surface of stent 1306 to cover runner 1330 as shown. A corresponding diamond-shaped suture pattern P1 may attach a perimeter of flap 1350 to struts 1320 forming row R1 of cells 1322 so that the bowing of runner 1330 pushes flap 1350 radially outward.

Panels 1352 formed of the same or different material than cuff 1322 may be coupled to all cells or to certain cells 1322 where folding is difficult. Specifically, panels 1352 may be coupled to cuff 1312 and/or struts 1320 of cells 1322 of row R1 located directly below commissure features 1325, while flaps 1350 may be provided for all other cells 1322 in row R1. Panels 1352 may be formed from segments of material that are initially not attached to cuff 1312, and may be attached to cells 1322 under commissure features 1325 using a diamond pattern of sutures similar to that of pattern P1. For the sake of clarity, only one panel 1352 is shown under the left-most commissure feature 1325*a* and no panels are shown under commissure features 1325*b*,1325*c* so that the shape of cuff 1312 may be appreciated. It will be understood, however, that panels 1352 may be coupled to cells 1322 located under commissure features 1325*b* and 1325*c*.

Figure 14:
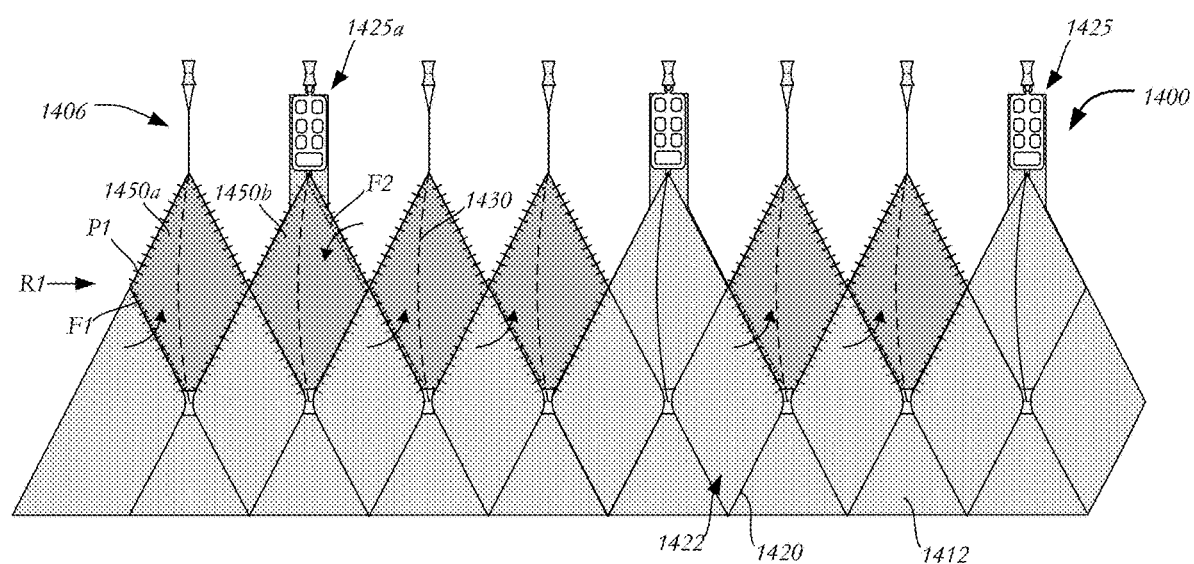

FIG. 14 is a schematic developed view of a portion of heart valve 1400 including stent 1406 and cuff 1412 attached to the stent. Stent 1406 includes struts 1420 forming cells 1422, commissure features 1425, and runners 1430. Heart valve 1400 includes first flaps 1450*a* that are similar to flaps 1350 of FIG. 13 described above. Heart valve 1400 differs from heart valve 1300 in that second flaps 1450*b* are also formed under commissure features 1425. Specifically, instead of panels that initially are separate from and later are attached to the cuff, cuff 1412 includes second flaps 1450*b* that fold 180 degrees at fold line F2 and then attach to cell 1422 under commissure feature 1425 to form two layers of cuff sandwiching runner 1430. For the sake of clarity, only one second flap 1450*b* is shown under commissure feature 1425*a*. Thus, cuff 1412 may be integrally formed from a single piece of material, disposed on the luminal surface of stent 1406 and include flaps on the abluminal surface to cover runners 1430.

Figure 15:
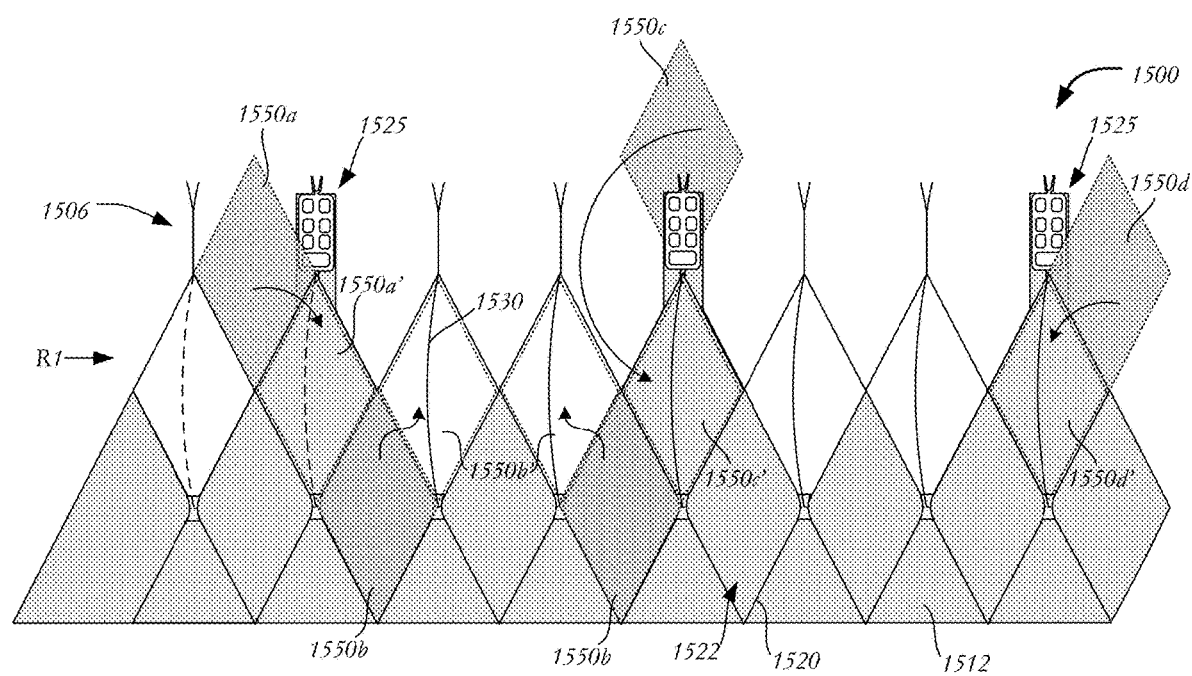

FIG. 15 is a similar developed view of a portion of heart valve 1500 including stent 1506 with cuff 1512 attached thereto. Stent 1506 includes struts 1520 forming cells 1522, commissure features 1525, and runners 1530. Various methods of folding flaps over runners 1530 are shown. In each example, flap 1550 is folded to a position over cell 1522 indicated by a diamond in broken lines. For example, flap 1550a is capable of folding diagonally downward to position 1550a', while flaps 1550b fold diagonally upward toward position 1550b'. Flap 1550c may fold straight down to position 1550c' and flap 1550d may fold diagonally downward to position 1550d'.

Figure 16A:
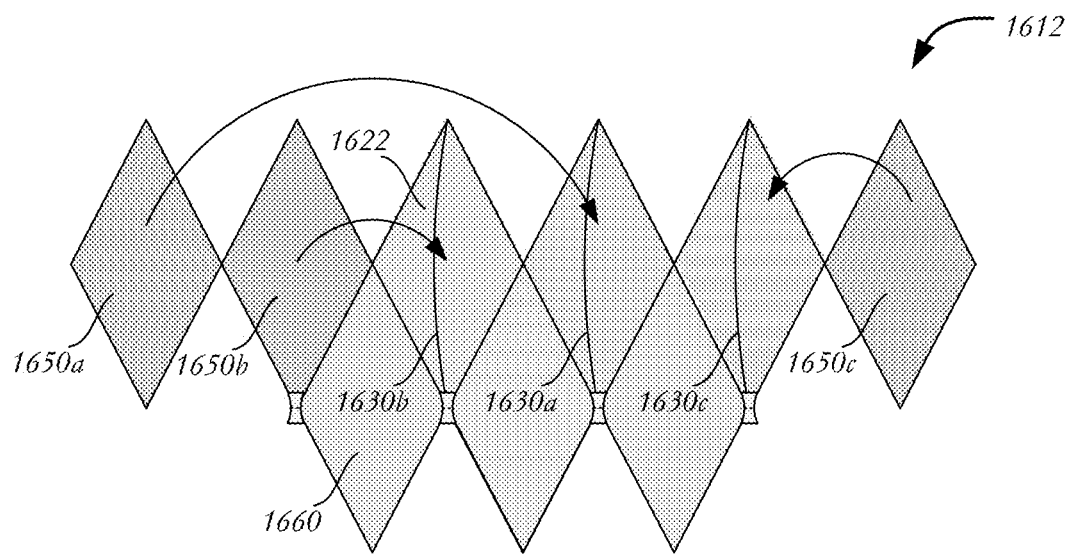
FIGS. 16A and 16B are highly schematic partial views of another method of folding a cuff over runners in a first row.
Figure 16B:
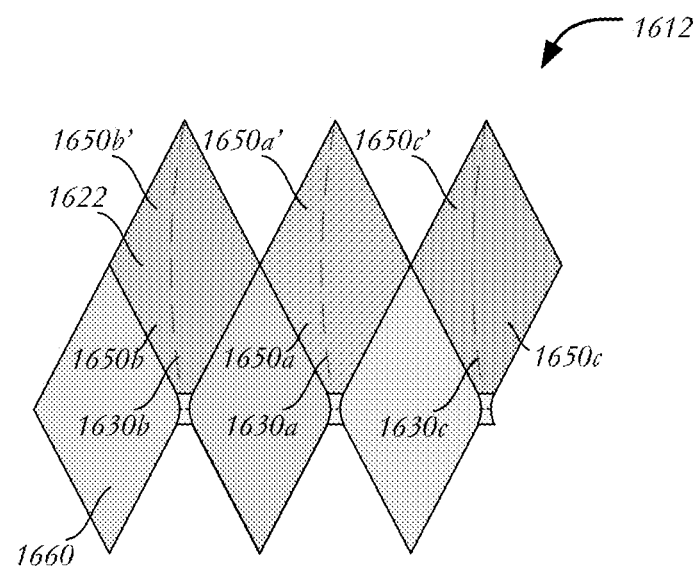

FIGS. 16A and 16B illustrate yet another example of cuff 1612 for covering a plurality of runners 1630 using flaps 1650. FIG. 16A illustrates the preassembled state in which cuff 1612 includes three flaps 1650a, 1650b and 1650c that will be horizontally folded over runners 1630 and main portion 1660 of the cuff that covers six cells 1622. Cuff 1612 may be formed of a single piece of material or may be formed as a composite cuff with multiple portions. For example, in FIG. 16A, first flap 1650a and second flap 1650b may be formed of a first piece of material, main portion 1660 may be formed of a second piece of material and third flap 1650c may be formed of a third piece of material. All three pieces may be sutured or otherwise coupled together to form a triple composite cuff.

As seen in the assembled state (FIG. 16B), first flap 1650a and second flap 1650b have been folded horizontally so that first flap 1650a extends to position 1650a' over first runner 1630a, and second flap 1650b extends to position 1650b' over second runner 1630b. Flap 1650c has been folded horizontally (in a direction opposite to first flap 1650a and second flap 1650b) to position 1650c' over third runner 1630c. Flaps 1650 may then be sutured to their respective cells around their perimeters In FIG. 17, heart valve 1700 includes stent 1706 and cuff 1712, as well as runners 1730 in row R1 of cells 1722. Instead of folding flaps as described above, individual panels 1750 are sutured around their perimeter to each cell 1722 in row R1 as shown. Panels 1750 may be formed of the same material as cuff 1712, or from a different material. Because runners 1730 bow outwardly, panels 1750 may be slightly larger than the underlying cells 1722, such as first panel 1750a, so as to not impede the outward bowing. Additionally, panels 1750 may be formed with a specific fiber orientation, compliance, thickness or the like to allow for the bowing. Pockets formed between cuff 1712 and panels 1750 may be filled with a liquid, a gel, a powder or other media to help support the outward bulging of the panels and thereby help mitigate paravalvular leakage. One example of the filler media may be a solution of polyvinyl alcohol (PVA). As cuff 1712 and panels 1750 contact blood upon the implantation of prosthetic heart valve 1700, the filler media may swell in size, increasing the size and specifically the diameter of the pockets between the cuff and the panels. The enlarged pockets thus fill the gaps between the native valve annulus and the prosthetic heart valve, minimizing or preventing paravalvular leakage.

Figure 17:
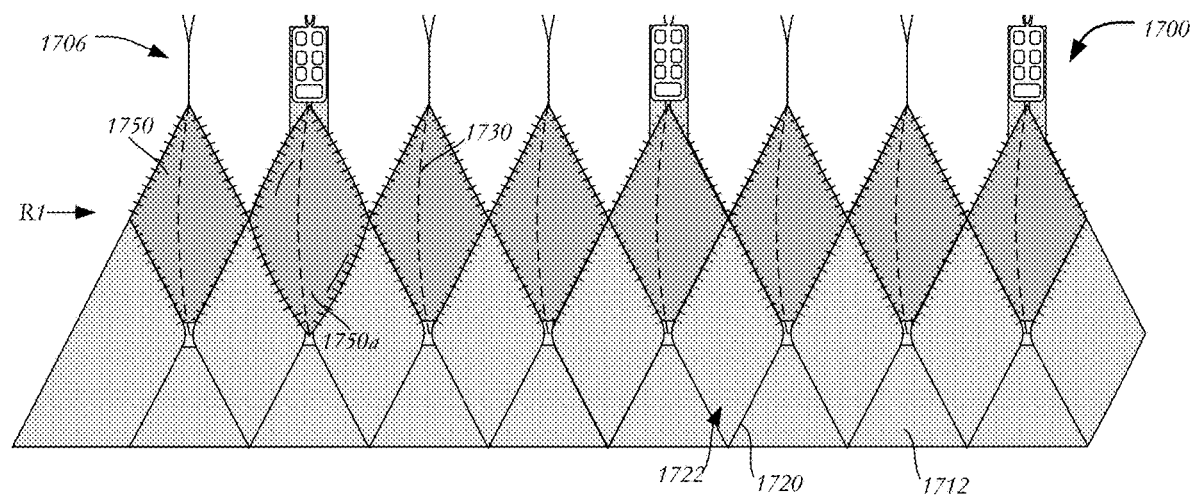
FIG. 17 is a highly schematic developed view of a portion of a heart valve having a cuff and individual panels attached over runners in a first row.
Figure 18:
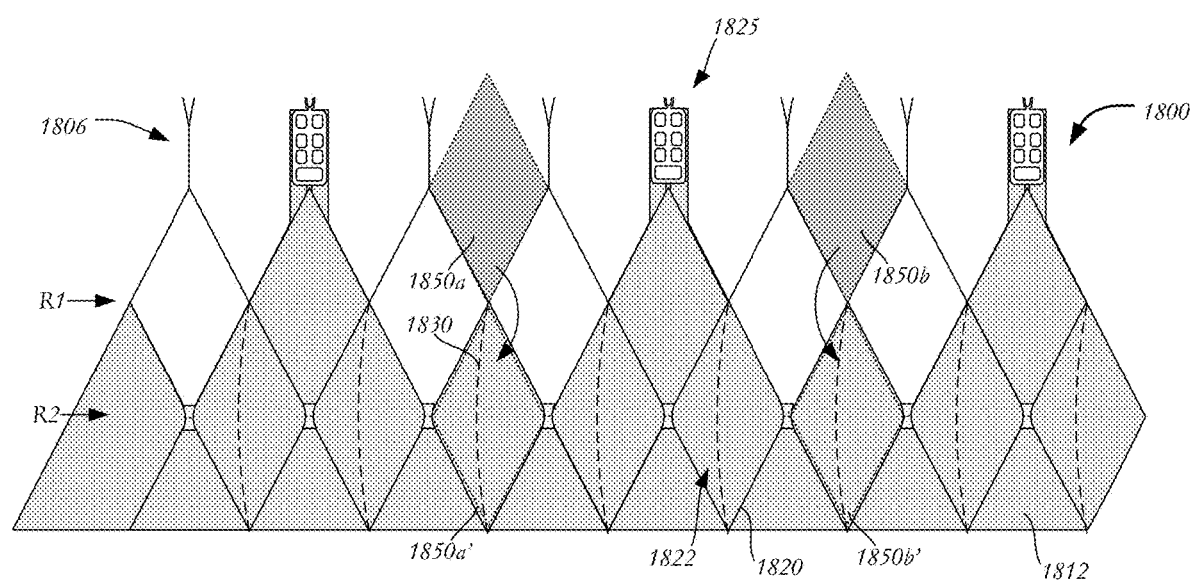
FIGS. 18-20 are highly schematic developed views of portions of heart valves including cuffs having folding flaps attached over runners in a second row.

FIG. 18 is a schematic developed view of a portion of heart valve 1800 including stent 1806 and cuff 1812 attached to the stent. Stent 1806 includes struts 1820 forming cells 1822, commissure features 1825, and runners 1830. In FIG. 15, runners 1330 were formed in each of cells 1322 in row R1 located directly below commissure features 1325. In the instant example, runners 1830 are provided in each of the cells in row R2 located in the second full row below commissure features 1825. Flaps 1850a and 1850b fold vertically downward to positions 1850a' and 1850b', respectively, sandwiching certain runners 1830 between cuff 1812 and the flaps. Other runners 1830 may be covered with individual panels (not shown) as described above with reference to FIG. 17.

Figure 19:
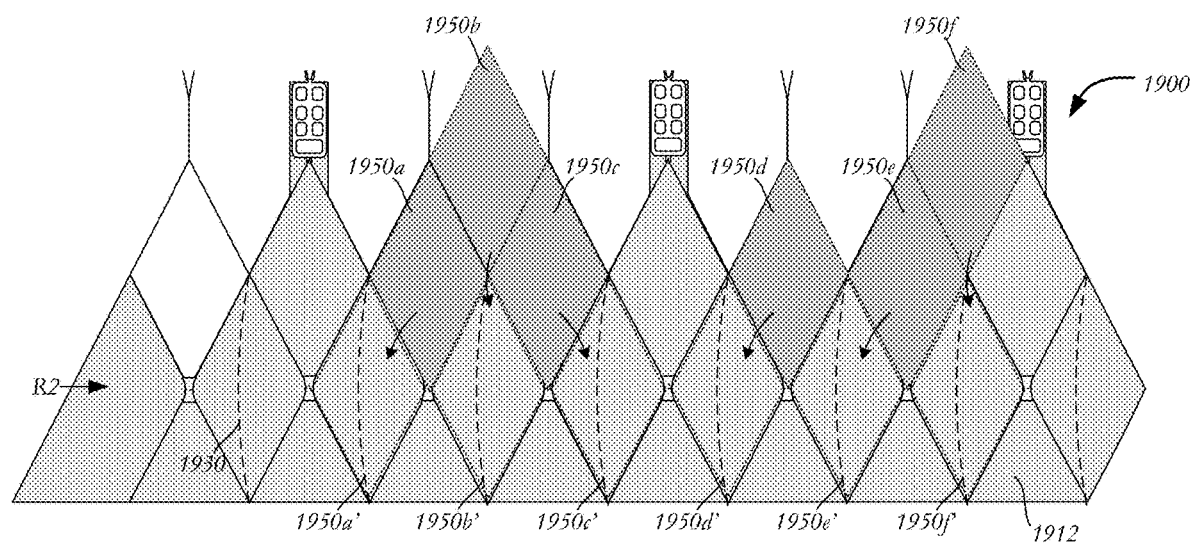
Figure 20:
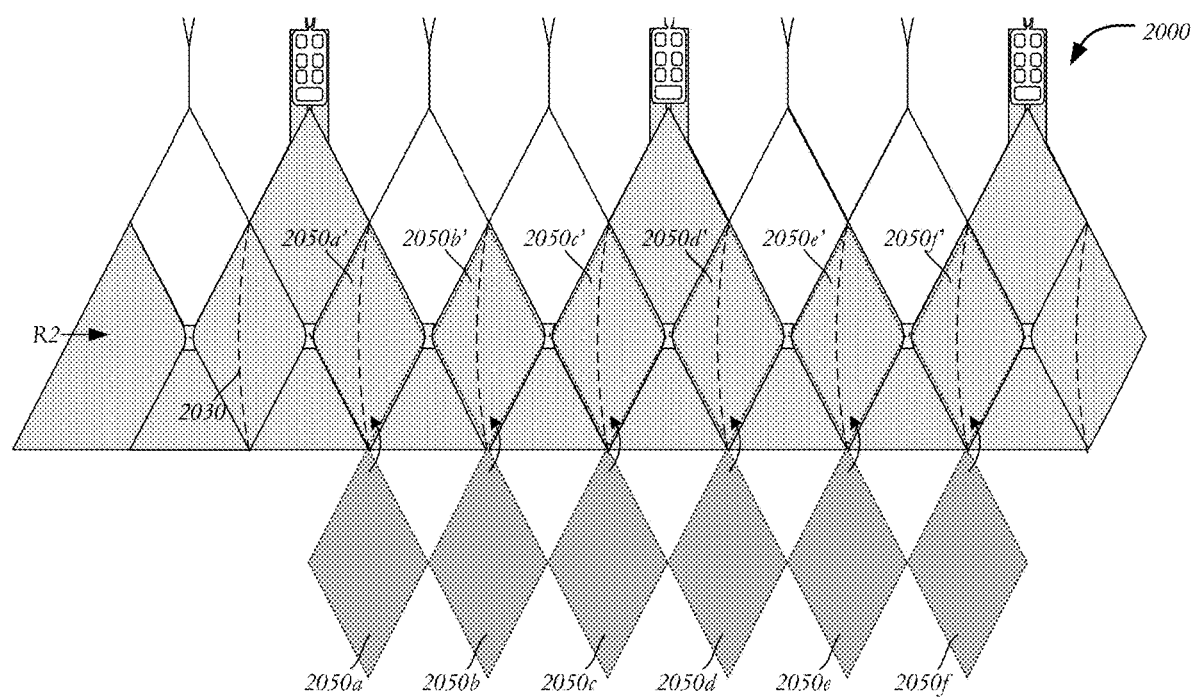

FIG. 19 illustrates another variation in which heart valve 1900 includes flaps 1950a-f which are arranged to fold over runners 1930 in row R2. Flaps 1950a-f may be unitarily formed with cuff 1912 and cut at certain edges depending on their intended position to create individual diamond-shaped flaps. Flaps 1950a-f may be folded either diagonally or vertically downward to positions 1950a'-f, respectively. In another variation of folding flaps over the runners in second row R2, FIG. 20 illustrates heart valve 2000 having runners 2030 and flaps 2050a-f that are foldable directly upward to the abluminal surface onto positions 2050a'-f as shown. In a further variation of the FIG. 20 embodiment, individual panels as shown in FIG. 17 may be disposed over each of runners 2030 in second row R2. Such panels may be enlarged or chosen based on specific properties as discussed above with reference to FIG. 17.

Figure 21:
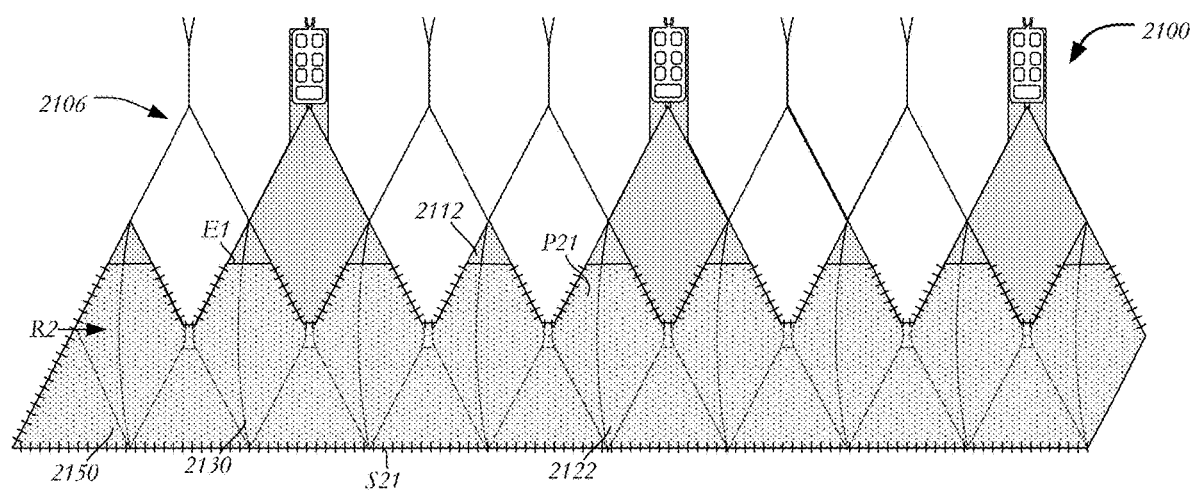
FIG. 21 is a highly schematic developed view of a portion of a heart valve including a cuff and a covering disposed over runners in a second row.

In FIG. 21, heart valve 2100 includes stent 2106 and attached cuff 2112. Stent 2106 includes a plurality of cells 2122 and runners 2130 in second row R2 of the cells. Cuff 2112 is attached to the luminal surface of stent 2106. Instead of individual panels or folded flaps, heart valve 2100 includes a unitary sheet of material 2150 coupled to the abluminal surface of stent 2106. Sheet 2150 may be sized to extend over all cells 2122 in second row R2 and may be attached to cuff 2112 using suture pattern s21. Suture pattern S21 extends around the perimeter of sheet 2150 with the exception of edges E1, which may be left unattached to cuff 2122. Blood flowing in a retrograde direction when heart valve 2100 is implanted in a patient may enter into a pocket P21 formed between sheet 2150 and cuff 2112 at edges E21 and causes the pocket to expand. In one variation of this embodiment, cuff 2112 and sheet 2150 may be unitarily formed such that a single piece of material is folded from the luminal surface over the bottom of the stent and forms a second layer on the abluminal surface of the stent. In one example, such a fold or transition may be made distal to the runners.

Figure 22A:
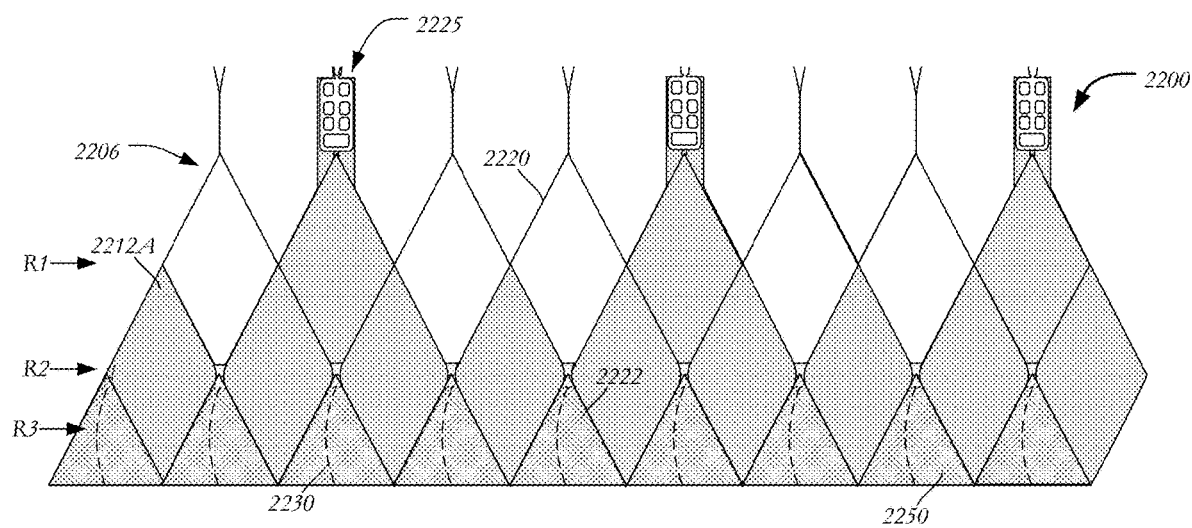
FIGS. 22A-24 are highly schematic developed views of portions of heart valves including cuffs having various folding flaps and panels for covering runners in a third row.
Figure 22B:
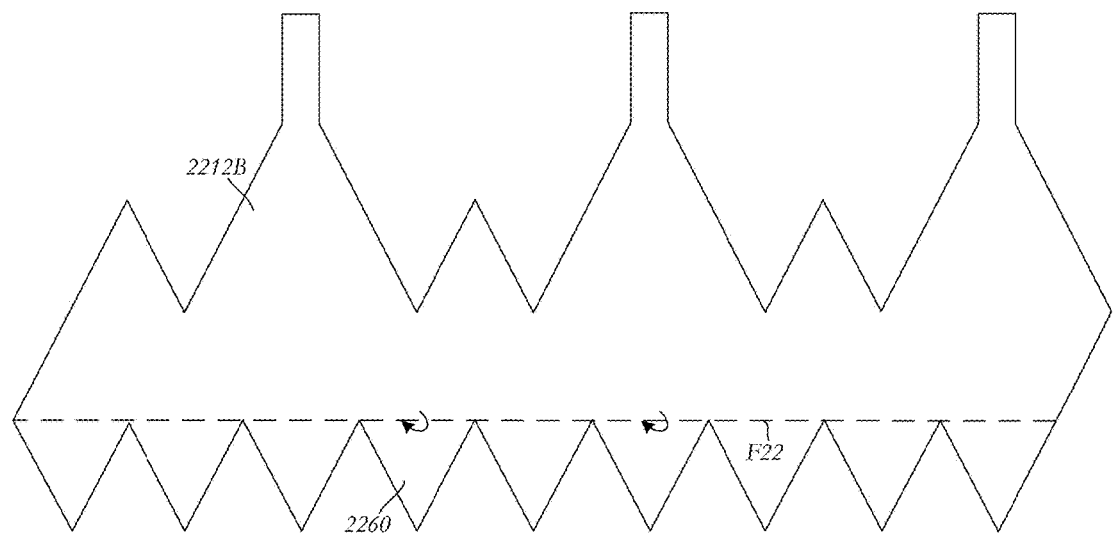

FIG. 22A is a schematic developed view of heart valve 2200 including stent 2206 and attached cuff 2212A. Stent 2206 includes struts 2220 forming cells 2222, commissure features 2225, and runners 2230. Three rows of cells, R1, R2, R3 are shown below commissure feature 2225. In this example, runners 2230 are disposed in row R3 of incomplete cells defined at the proximal end of stent 2206, and are attached to the bottom-most struts 2220 of stent 2206 in a manner similar to the stent described in connection with the embodiment of FIG. 11C. Individual panels 2250 may be sutured over each portion of a cell having a runner. In a slight variation, shown in FIG. 22B, cuff 2212B may be disposed on the luminal surface of a stent (not shown) and include a plurality of triangular flaps 2260 that may be folded upwardly at fold line F22 and extend over the runners on the abluminal surface of the stent. Thus, flaps 2260 may take the place of individual panels 2250 from FIG. 22A.

Figure 23:
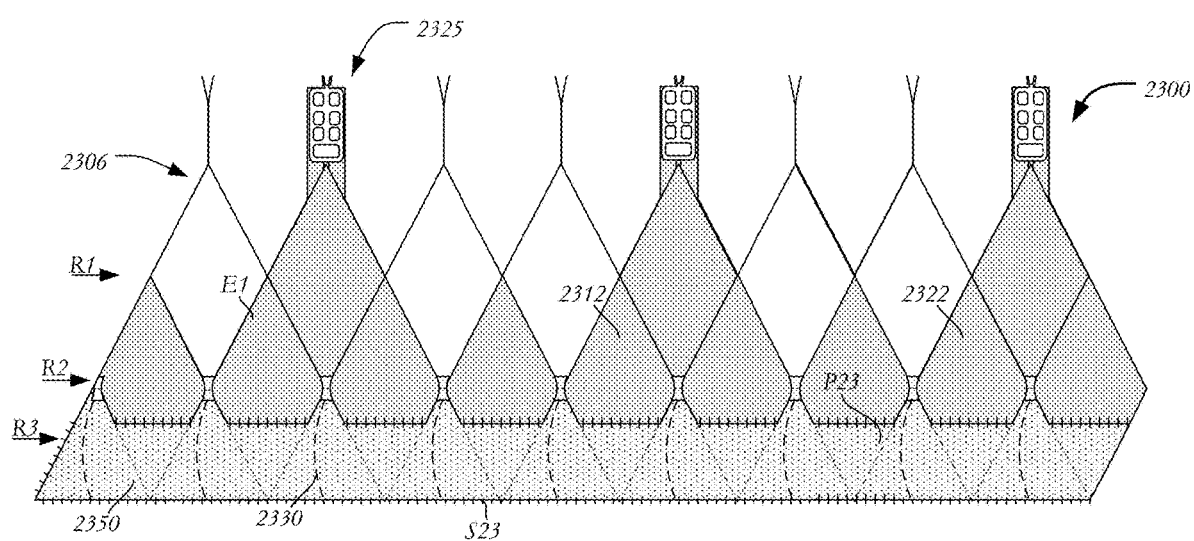

In FIG. 23, heart valve 2300 includes stent 2306 and attached cuff 2312. Stent 2306 includes a plurality of cells 2322 arranged in three rows, R1, R2, R3 below commissure feature 2325. Runners 2330 are disposed in row R3 of incomplete cells 2322 at the proximal end of the stent. Cuff 2312 is attached to the luminal surface of stent 2306. Heart valve 2300 further includes a unitary sheet of material 2350 coupled to the abluminal surface of stent 2306 so as to overlie runners 2330. Sheet 2350 may be sized to extend over all incomplete cells 2322 in row R3 and may be attached to cuff 2312 using a stitch pattern S23 around the perimeter of sheet 2350. Thus, cuff 2312 and sheet 2350 may form a continuous pocket P23, which functions similarly to individual pockets P21 of FIG. 21 described above.

Figure 24:
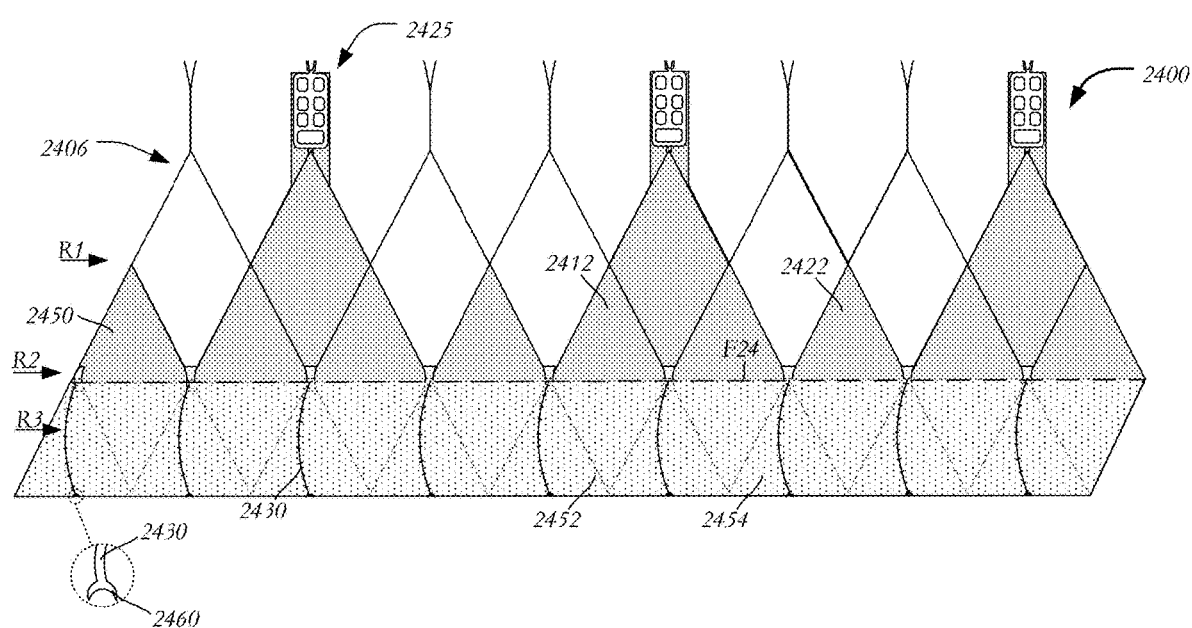

FIG. 24 illustrates heart valve 2400 including stent 2406 and attached cuff 2412. Stent 2406 includes a plurality of cells 2422 arranged in three rows, R1, R2, R3 below commissure feature 2425. Runners 2430 are disposed in third row R3 of incomplete cells 2422 at the proximal end of the stent. Instead of a unitary sheet of material or individual panels, cuff 2412 includes upper portion 2450 and lower portion 2452 and fold line F24 separating the two portions. Fold line F24 is disposed along the tops of the incomplete cells in third row R3. Lower portion 2452 is divided into individual, substantially rectangular segments 2454. Upper portion 2450 is attached to the luminal surface of stent 2406. At fold line F24, rectangular segments 2454 may be folded from the luminal surface to the abluminal surface of stent 2406, each segment passing through the center of cell 2412. Segments 2454 of lower portion 2452 may then be stitched to adjacent segments and to runners 2430. To aid in securing segments 2454 of lower portion 2452, each runner 2430 may include a horseshoe 2460 at its free end and segments 2454 may be sutured to horseshoes 2460, which may prevent lower portion 2452 from riding up runner 2430 during assembly or use. In some variations, eyelets or other similar features may be disposed at the free ends of the runners. Thus, a portion of cuff 2412 is disposed on the luminal surface of stent 2406 and a second portion of cuff 2412 is disposed over runners 2430 and on the abluminal surface of stent 2406.

While the devices disclosed herein have been described for use in connection with heart valve stents having a particular shape, the stent could have different shapes, such as a flared or conical annulus section, a less-bulbous aortic section, and the like, as well as a differently shaped transition section. Additionally, though the runners and cuffs have been described in connection with expandable transcatheter aortic valve replacement, they may also be used in connection with other expandable cardiac valves, as well as with surgical valves, sutureless valves and other devices in which it is desirable to create a seal between the periphery of the device and the adjacent body tissue.

Moreover, although the disclosures herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present claims.

In some embodiments, a prosthetic heart valve for replacing a native valve includes a stent extending between a proximal end and a distal end and including a plurality of struts forming cells, the stent having a collapsed condition and an expanded condition. At least one runner is coupled to a cell, the at least one runner being configured to transition from a first configuration to a second configuration when the stent moves from the collapsed condition to the expanded condition, the at least one runner projecting radially outwardly from the cell in the second configuration. A valve assembly is disposed within the stent, the valve assembly including a plurality of leaflets, a cuff at least partially disposed on a luminal surface of the stent and a covering material disposed on an abluminal surface of the stent and covering the at least one runner in the second configuration.

In some examples, the at least one runner is substantially linear in the first configuration, and/or the at least one runner is bowed in the second configuration, and/or the cuff includes at least one flap configured to fold from the luminal surface to the abluminal surface of the stent to form the covering material, and/or the flap folds over a selected strut from the distal end toward the proximal end of the stent, and/or the flap folds over a selected strut from the proximal end toward the distal end of the stent, and/or the flap folds diagonally over a selected strut, and/or the at least one runner comprises multiple runners and the covering material includes a plurality of individual panels, each of the plurality of individual panels being disposed over one of the multiple runners, and/or the covering material includes at least one diamond-shaped panel disposed over at least one cell, and at least one flap integrally formed with the cuff and configured to fold from the luminal surface to the abluminal surface of the stent, and/or the stent further includes commissure features and the at least one runner coupled to selected cells in a first row of the cells proximal of the commissure features, and/or the stent further includes commissure features and the at least one runner coupled to selected cells in a second row of the cells proximal of the commissure features, and/or a plurality of runners coupled to proximal-most struts of the stent and extending proximally of the proximal end of the stent, and/or each of the plurality of runners extends from a first end joined to a strut to a free end, and/or each free end has a horseshoe shape, the covering material being sutured to the horseshoe shape, and/or the covering material includes a sheet of material circumferentially disposed on the abluminal surface of the stent so as to extend over a row of cells.

In some embodiments, a prosthetic heart valve for replacing a native valve includes a stent extending between a proximal end and a distal end and including a plurality of struts forming cells and a plurality of runners, the stent having a collapsed condition and an expanded condition, the struts defining a first diameter and the runners defining a second diameter, the second diameter being greater than the first diameter. A valve assembly is disposed within the stent, the valve assembly including a plurality of leaflets and a cuff at least partially disposed on a luminal surface of the stent and partially disposed on an abluminal surface of the stent to cover the runner.

In some examples, the stent includes a plurality of commissure features and the cuff includes an upper portion and a lower portion, the upper portion being disposed on the luminal surface of the stent and coupled to the commissure features and the lower portion being disposed on the abluminal surface of the stent so as to cover the plurality of runners, and/or the lower portion is divided into individual segments capable of passing through the cells from the luminal surface to the abluminal surface, and/or the cuff transitions from the luminal surface to the abluminal surface distal to the plurality of runners, and/or each of the individual segments is coupled to an adjacent segment and a runner.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve for replacing a native valve, comprising:
    a stent extending between a proximal end and a distal end along a longitudinal axis, the stent having a collapsed condition and an expanded condition and including a plurality of struts forming cells;

a valve assembly comprising a plurality of leaflets disposed within the stent and at least partially coupled to a luminal surface of the stent, and a cuff disposed on an abluminal surface of the stent and defining an inflow of the valve assembly and an outflow of the valve assembly, the cuff having foldable portions to form an inner layer and an outer layer; and at least one runner coupled to a respective cell of the stent, the at least one runner being configured to transition from a first configuration to a second configuration when the stent moves from the collapsed condition to the expanded condition, wherein the at least one runner is sandwiched between the inner layer of the cuff and the outer layer of the cuff and pushes the outer layer of the cuff radially outward when the at least one runner transitions from the first configuration to the second configuration.

2. The prosthetic heart valve of claim 1, wherein each of the cells include a lower vertex adjacent the proximal end, an upper vertex adjacent the distal end, and two side vertices disposed longitudinally between the upper vertex and the lower vertex.

3. The prosthetic heart valve of claim 2, wherein the at least one runner has first and second ends coupled to the opposing vertices of one of the cells.

4. The prosthetic heart valve of claim 1, wherein the at least one runner is substantially linear in the first configuration and is parallel to the longitudinal axis of the stent.

5. The prosthetic heart valve of claim 1, wherein the at least one runner is bowed or curved in the second configuration.

6. The prosthetic heart valve of claim 1, wherein the at least one runner projects radially outwardly from one of the cells in the second configuration.

7. The prosthetic heart valve of claim 1, wherein the at least one runner is disposed radially outward of the leaflets.

8. The prosthetic heart valve of claim 1, wherein the stent has a length direction between the proximal end and the distal end, and the at least one runner extends substantially in the length direction in the second configuration.

9. The prosthetic heart valve of claim 1, wherein the at least one runner extends substantially in a circumferential direction of the stent in the second configuration.

10. The prosthetic heart valve of claim 1, wherein the stent further includes commissure features.

11. The prosthetic heart valve of claim 1, wherein the cuff is foldable in a horizontal direction to sandwich the at least one runner.

12. The prosthetic heart valve of claim 1, wherein the cuff is foldable in a vertical direction to sandwich the at least one runner.

13. The prosthetic heart valve of claim 1, wherein the cuff is foldable in a diagonal direction to sandwich the at least one runner.

14. The prosthetic heart valve of claim 1, wherein the cuff includes multiple flaps that are foldable in different directions.

15. A prosthetic heart valve for replacing a native valve, comprising:

a stent extending between a proximal end and a distal end along a longitudinal axis, the stent having a collapsed condition and an expanded condition and including a plurality of struts forming diamond shaped cells in the expanded condition;

a valve assembly disposed within the stent and at least partially coupled to a luminal surface of the stent, and cuff disposed on an abluminal surface of the stent and defining an inflow of the valve assembly and an outflow of the valve assembly, the cuff having foldable portions to form an inner layer and an outer layer; and at least one runner coupled to a respective cell of the stent, the at least one runner being configured to transition from a first configuration to a second configuration when the stent moves from the collapsed condition to the expanded condition, wherein the at least one runner is sandwiched between the inner layer of the cuff and the outer layer of the cuff and pushes the outer layer of the cuff radially outward when the at least one runner transitions from the first configuration to the second configuration.

16. The prosthetic heart valve of claim 15, wherein each of the cells include a lower vertex adjacent the proximal end, an upper vertex adjacent the distal end, and two side vertices disposed longitudinally between the upper vertex and the lower vertex.

17. The prosthetic heart valve of claim 16, wherein the at least one runner has first and second ends coupled to the opposing vertices of one of the cells.

18. The prosthetic heart valve of claim 15, wherein the at least one runner is substantially linear in the first configuration and is parallel to the longitudinal axis of the stent.

19. The prosthetic heart valve of claim 15, wherein the at least one runner is bowed or curved in the second configuration.

20. The prosthetic heart valve of claim 15, wherein the at least one runner projects radially outwardly from the one of the cells in the second configuration.

* * * * *